(12) United States Patent
Bower et al.

(10) Patent No.: US 9,177,102 B2
(45) Date of Patent: Nov. 3, 2015

(54) DATABASE AND IMAGING PROCESSING SYSTEM AND METHODS FOR ANALYZING IMAGES ACQUIRED USING AN IMAGE ACQUISITION SYSTEM

(75) Inventors: Bradley A. Bower, Hillsborough, NC (US); Eric L. Buckland, Hickory, NC (US); Kenneth W. Chapman, Raleigh, NC (US); Igor Touzov, Cary, NC (US)

(73) Assignee: Bioptigen, Inc., Durham, NC (US)

( * ) Notice: Subject to any disclaimer, the term of this patent is extended or adjusted under 35 U.S.C. 154(b) by 473 days.

(21) Appl. No.: 13/459,866

(22) Filed: Apr. 30, 2012

(65) Prior Publication Data

US 2012/0275677 A1  Nov. 1, 2012

Related U.S. Application Data

(60) Provisional application No. 61/480,189, filed on Apr. 28, 2011.

(51) Int. Cl.
*G06K 9/00* (2006.01)
*G06F 19/00* (2011.01)
*G06T 7/00* (2006.01)
*A61B 3/10* (2006.01)

(52) U.S. Cl.
CPC ............ *G06F 19/321* (2013.01); *G06T 7/0012* (2013.01); *A61B 3/102* (2013.01); *G06T 2207/10101* (2013.01); *G06T 2207/30041* (2013.01)

(58) Field of Classification Search
None
See application file for complete search history.

(56) References Cited

U.S. PATENT DOCUMENTS

| | | | |
|---|---|---|---|
| 6,112,194 A | 8/2000 | Bigus | |
| 7,539,927 B2 | 5/2009 | Lee et al. | |
| 7,594,889 B2 | 9/2009 | St. Ores et al. | |
| 7,627,620 B2 | 12/2009 | Campos et al. | |
| 7,752,057 B2 | 7/2010 | Ikeguchi et al. | |
| 2002/0186818 A1* | 12/2002 | Arnaud et al. | 378/165 |
| 2006/0062442 A1* | 3/2006 | Arnaud et al. | 382/128 |
| 2007/0287932 A1* | 12/2007 | Huang et al. | 600/558 |
| 2008/0181477 A1* | 7/2008 | Izatt et al. | 382/128 |
| 2008/0279439 A1* | 11/2008 | Minyard et al. | 382/131 |
| 2011/0137156 A1 | 6/2011 | Razzaque et al. | |
| 2011/0169978 A1 | 7/2011 | Lasser et al. | |
| 2013/0015975 A1 | 1/2013 | Huennekens et al. | |
| 2013/0271757 A1 | 10/2013 | Kang et al. | |

\* cited by examiner

*Primary Examiner* — Atiba O Fitzpatrick

(74) *Attorney, Agent, or Firm* — Myers Bigel Sibley & Sajovec

(57) ABSTRACT

Methods are provided including receiving a plurality of images from at least one image acquisition system; selecting at least a portion of a set of images for analysis using at least one attribute of image metadata; selecting at least one method for deriving quantitative information from the at least a portion of the set of images; processing the selected at least a portion of the set of images with the selected at least one method for deriving quantitative information; associating the derived quantitative information with the at least a portion of the set of images via a data structure; selecting at least one method for aggregating at least a portion of a set of derived quantitative information into a reduced set of results; and generating at least one report to represent the reduced set of results for one of an individual image and the set of images as a pool.

15 Claims, 19 Drawing Sheets

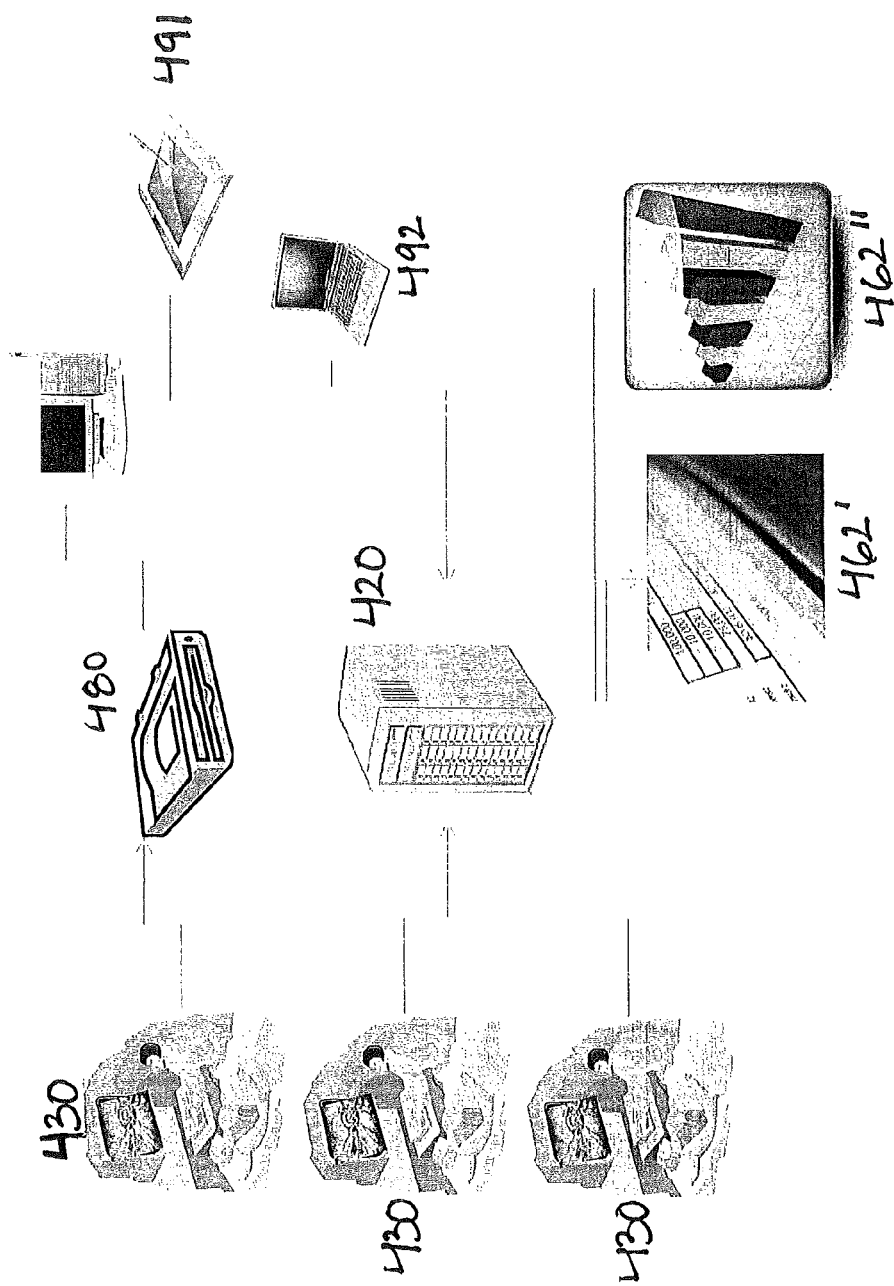

| Study | Primary | |
|---|---|---|
| | Substudy | |
| Investigators | Principal | |
| | Collaborators | |
| | Technicians | |
| Subjects | Controls | |
| | Treatment Arm a | |
| | Treatment Arm b | |
| | Treatment Arm z... | |
| Metadata | Subject Demographics | Subject Specific |
| | | Geographical |
| | | Population |
| | Treatments | Study Related |
| | | Study Unrelated |
| | Diagnoses | Study Related |
| | | Study Unrelated |
| | Other Conditions | |
| Procedures | Laser | |
| | Surgical | |
| | Pharmaceutical | |
| Time | Baseline | |
| | t1 | |
| | t2 | |
| | tn... | |
| Image Data | Image Type | |
| | Image Parameters | |

| Image Processing | Methods | Segmentation |
|---|---|---|
| | | Volumetrics |
| | | Texture Analysis |
| | | Histograms |
| | | Functional |
| | Display | Segments |
| | | Thickness Maps |
| | | Texture Maps |
| | | Projections |
| Analysis | Image Statistics | |
| | Diagnostic Grades | |
| | Specialist Findings | |
| | Annotations | |
| Study Statistics | Population Statistics | |
| | ANOVA | |
| Queries | HyperCube | |
| Reports | Sample Reports | |
| | Image Collections | |
| | Sample Data | |
| | Population Data | |
| | Study Data | |
| Aggregations | Normative Data | |
| | Longitudinal Progressions | |
| | Demographic | |
| Mining | Custom Queries | |

Figure 5

| | | |
|---|---|---|
| Databases | Metadata | |
| | Image Processing Results | |
| | Diagnoses and Inferences | |
| Image Files | OCT | |
| | Fundus Photos | |
| | Endo Photos | |
| | Spectroscopic | |
| | MRI | |
| | Ultrasound | |
| | CT | |
| | PET | |
| Storage | Local Drives | |
| | External Drives | |
| | Servers | |
| | Coud | |
| Communications | USB | |
| | Firewire | |
| | Wireless | |
| | Ethernet | |
| Outputs | Raw Images | |
| | Raw Analysis | |
| | Aggregated Data by Sector | |
| | Coordinate graphs | |
| | Heat Maps | |
| | Intensity Projections | |
| | Histograms | |
| | Spreadsheets | |
| | DICOM | |
| | SAS | |

Figure 6

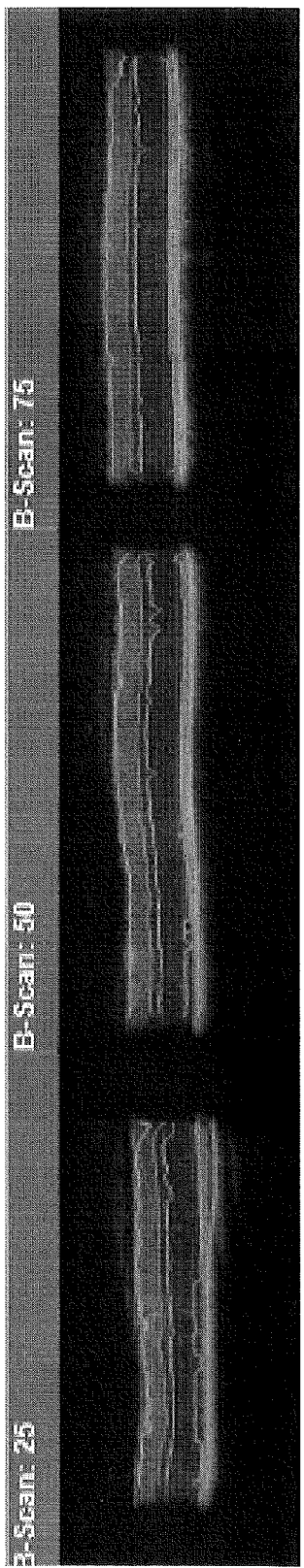
Figure 14
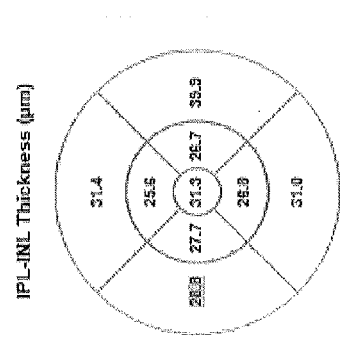
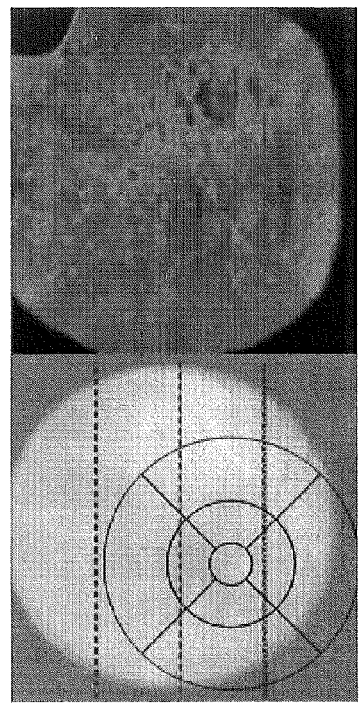
Figure 15

US 9,177,102 B2

DATABASE AND IMAGING PROCESSING SYSTEM AND METHODS FOR ANALYZING IMAGES ACQUIRED USING AN IMAGE ACQUISITION SYSTEM

CLAIM OF PRIORITY

The present application claims priority from U.S. Provisional Application No. 61/480,189, filed Apr. 28, 2011, the disclosure of which is hereby incorporated herein by reference as if set forth in its entirety.

FIELD

The present invention relates to imaging and, more particularly, to as system for analysis of images and related methods and computer program products.

BACKGROUND

Data mining is a technique by which patterns may be identified in seemingly unstructured data. This data can be any type of data, for example, data mining is often used in the medical field so that information associated with a single patient, or group of patients, may be located in existing databases of unstructured data. Data mining techniques are discussed in, for example, U.S. Pat. Nos. 6,112,194; 7,539,927; 7,594,889; 7,627,620; and 7,752,057, the disclosures of which are hereby incorporated herein by reference as if set forth in their entirety.

As discussed above, one area where there is an ever increasing need to identify patterns in unstructured data is in the medical field. Medical data exists in various forms, for example, patient histories and demographic data, clinical and lab results, images (computed tomography (CT) scans, ultrasounds, magnetic resonance imaging (MRI), positron emission tomography (PET) scans and the like), billing information and insurance codes. Just imaging systems and assays alone produce a tremendous amount of relatively unstructured data. As discussed above, many conventional data mining techniques are available to locate patterns in this vast amount of unstructured data so that more accurate diagnoses may be provided and more subtle markers of disease and disease progression may be identified.

SUMMARY

Some embodiments of the present inventive concept provide methods for analyzing images acquired using an image acquisition system. The method includes receiving a plurality of images from at least one image acquisition system; selecting at least a portion of a set of images for analysis using at least one attribute of image metadata; selecting at least one method for deriving quantitative information from the at least a portion of the set of images; processing the selected at least a portion of the set of images with the selected at least one method for deriving quantitative information; associating the derived quantitative information with the at least a portion of the set of images via a data structure; selecting at least one method for aggregating at least a portion of a set of derived quantitative information into a reduced set of results; and generating at least one report to represent the reduced set of results for one of an individual image and the set of images as a pool.

In further embodiments, the at least one images acquisition system may be at least one Optical Coherence Tomography (OCT) imaging system. In certain embodiments, the at least one OCT imaging system may be at least one Fourier Domain Optical Coherence Tomography imaging System.

In still further embodiments, the image metadata may include one or more of: a patient demographic data; an individual responsible for drawing inferences from the data; an individual responsible for acquiring the images; a window of time for acquiring the images; a position in a sequence of events along which images may be acquired; a descriptor of instruments that may be used to acquire the image data; a descriptor of instrument settings used to acquire an image; a descriptor of image quality associated with an image; quantitative results derived from the image; an inference applied to the image; and an annotation associated with an image.

In some embodiments, the method may further include one or more of a marking, a structural measurement, a functional measurement, a descriptor, and an annotation.

In further embodiments, the method may further include one of a method involving user intervention with a representation of the image displayed on graphical display; a method that is fully automated through computer algorithms without user intervention; and a method including a combination of user intervention and computer algorithms.

In still further embodiments, the method may further include one of identifying a boundary of a layer, an area and a volume within the structure of the image.

In some embodiments, the method may further include identifying one or more regions of relative motion within the structure of the image.

In further embodiments, the method may include computing a flow within a region represented by the image.

In still further embodiments, the method may further include computing a descriptor of a portion of an image, wherein the descriptor may be one or more of a signal-to-noise ratio, an average noise, a noise variance, a distortion, an attribute histogram and a texture map.

In some embodiments, the reduced set of results may include a measurement of distances between boundaries identified within the structure of an image.

In further embodiments, the data structure may include one or more of a database, a file structure, and a spreadsheet.

In still further embodiments, the reduced set of results may include a statistical summarization of the measurement data according to a sector map defined for the image. In certain embodiments, the statistical summarization may include one or more of a count, an average, a variance, a standard deviation, and a higher order moment.

In some embodiments, the statistical summarization may include the computation of a confidence interval for the reduced results.

In further embodiments, the report may be derived from pooled statistical results from more than one image drawn from the image set.

In still further embodiments, the sector map may include one or more of a regular grid, a volumetric matrix, and a defined grid associated with a clinical or other standard.

In some embodiments, the report may include one or more of a data table; a two dimensional projection of volumetric data onto a plane; heat map that associates a color or a grayscale map to a two dimensional projection of reduced data values onto a plane; a spreadsheet of values derived from the image; and a spreadsheet of reduced values derived from image.

In further embodiments, the at least one image acquisition system may include at least one Fourier Domain Optical Coherence Tomography imaging System and wherein the Fourier Domain Optical Coherence Tomography images are images of a region of an eye.

In still further embodiments, the region of the eye may be selected from one of an anterior segment, cornea, a sclera, a crystalline lens, an iris, an iridocorneal angle, an implanted intraocular lens, a posterior segment, a retina, a macula, an optic nerve head, and a peripheral retina.

Some embodiments of the present inventive concept also provide related systems and computer program products.

BRIEF DESCRIPTION OF THE DRAWINGS

FIG. 4 is block diagram illustrating various details of the block diagram of FIG. 3 in accordance with some embodiments of the present inventive concept.

FIG. 5 is a chart illustrating various types of data that may be used by the image analysis system in accordance with some embodiments of the present inventive concept.

FIG. 6 is a chart illustrating various types of data that may be used by the image analysis system in accordance with some embodiments of the present inventive concept.

FIG. 14 is a diagram illustrating a multi-layer segmentation scans produced using an imaging analysis system in accordance with some embodiments of the present inventive concept.

FIG. 15 is a diagram illustrating thickness maps produced using an imaging analysis system in accordance with some embodiments of the present inventive concept.

DETAILED DESCRIPTION

Figure 1:
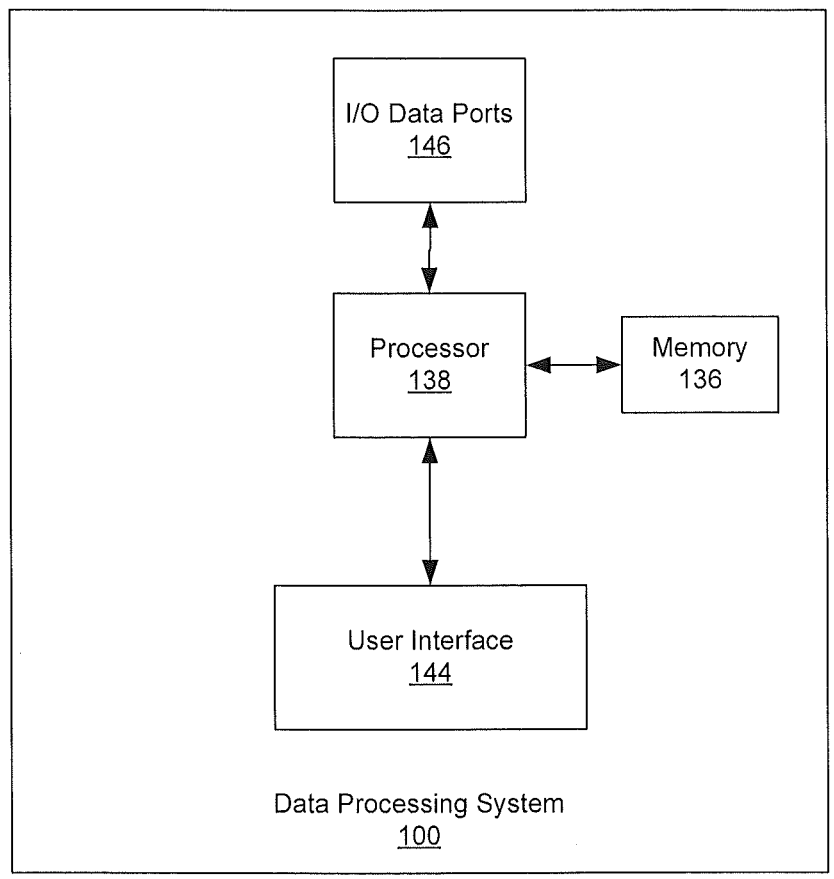
FIG. 1 is a block diagram of a data processing system suitable for use in some embodiments of the present inventive concept.

The present inventive concept will be described more fully hereinafter with reference to the accompanying figures, in which embodiments of the inventive concept are shown. This inventive concept may, however, be embodied in many alternate forms and should not be construed as limited to the embodiments set forth herein.

Accordingly, while the inventive concept is susceptible to various modifications and alternative forms, specific embodiments thereof are shown by way of example in the drawings and will herein be described in detail. It should be understood, however, that there is no intent to limit the inventive concept to the particular forms disclosed, but on the contrary, the inventive concept is to cover all modifications, equivalents, and alternatives falling within the spirit and scope of the inventive concept as defined by the claims. Like numbers refer to like elements throughout the description of the figures.

The terminology used herein is for the purpose of describing particular embodiments only and is not intended to be limiting of the inventive concept. As used herein, the singular forms "a", "an" and "the" are intended to include the plural forms as well, unless the context clearly indicates otherwise. It will be further understood that the terms "comprises", "comprising," "includes" and/or "including" when used in this specification, specify the presence of stated features, integers, steps, operations, elements, and/or components, but do not preclude the presence or addition of one or more other features, integers, steps, operations, elements, components, and/or groups thereof. Moreover, when an element is referred to as being "responsive" or "connected" to another element, it can be directly responsive or connected to the other element, or intervening elements may be present. In contrast, when an element is referred to as being "directly responsive" or "directly connected" to another element, there are no intervening elements present. As used herein the term "and/or" includes any and all combinations of one or more of the associated listed items and may be abbreviated as "/".

Unless otherwise defined, all terms (including technical and scientific terms) used herein have the same meaning as commonly understood by one of ordinary skill in the art to which this inventive concept belongs. It will be further understood that terms used herein should be interpreted as having a meaning that is consistent with their meaning in the context of this specification and the relevant art and will not be interpreted in an idealized or overly formal sense unless expressly so defined herein.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element without departing from the teachings of the disclosure. Although some of the diagrams include arrows on communication paths to show a primary direction of communication, it is to be understood that communication may occur in the opposite direction to the depicted arrows.

As discussed above, data mining techniques are being developed to provide more accurate diagnosis of disease. Accordingly, some embodiments of the present inventive concept provide method, systems and computer program products for identifying patterns in unstructured image data, which may be subsequently mined and analyzed as will be discussed further herein.

Although some embodiments of the present invention will be discussed herein with respect to Optical Coherence Tomography (OCT), it will be understood that other imaging techniques may be used without departing from the scope of the present inventive concept. For example, the images used in the methods, systems and computer program products discussed herein may be computed tomography (CT), ultrasound, magnetic resonance imaging (MRI), positron emission tomography (PET) images or any other type of image that may be used in combination with one or more of the embodiments discussed herein.

Furthermore, although many of the examples discussed herein refer to the sample being an eye, specifically, the retina, cornea, anterior segment and lens of the eye, embodiments of the present inventive concept are not limited to this type of sample. Any type of sample that may be used in conjunction with embodiments discussed herein may be used without departing from the scope of the present inventive concept.

In particular, the image analysis system in accordance with some embodiments of the present inventive concept is configured to automate analysis of retinal layers of mouse models acquired using spectral domain optical coherence tomography (OCT) imaging systems. The image analysis system may be configured to automatically detect boundaries in the layered structure of the retina in order to segment multiple discrete layers of the rodent retina, for example, 8 boundary for the segmentation of 7 layers; aggregate thickness results into a common early treatment diabetic retinopathy study (ET-DRS)-like grid; and generate graphical reports, thickness maps and intensity projections of all available layers. Thus, some embodiments of the present inventive concept may allow better visualization and quantification of findings related to retinal disease progression and therapeutic modalities, without requiring increased user intervention as will be discussed further herein.

Some embodiments of the present inventive concept may enable high throughput analysis of large datasets for both prospective and retrospective studies. Thus, embodiments of the present inventive concept may advance a researcher's ability to quantify, validate, and publish results more rapidly and less laboriously than is currently possible with conventional methods of managing image data, for example, OCT imaging date. Such methods, systems and computer program products may open new avenues for biological exploration, monitoring of disease progression, and development of therapeutic interventions as will be discussed further herein.

In the field of ophthalmology, optical coherence tomography (OCT) has become a standard of care. The advent of high speed Fourier domain OCT (FDOCT) has enabled the very rapid acquisition of volumetric images of the retina, cornea, anterior segment and lens of the eye. Such images may contain $10^8$ voxels of 16-bit images, and occupy files of 200 MB. The structures of the eye exhibit finely layered features, well visualized by FDOCT. The use of FDOCT has evolved from purely qualitative use, for example, answering the question—"can I see a pathology"—to limited quantitative use, for example, answering the question—"can I measure the retinal thickness." In clinical practice today, there are only two specified end points: total retinal thickness and retinal nerve fiber layer thickness.

Commercial clinical systems tend to have embedded segmentation algorithms to extract the three boundary layers required to measure the two thicknesses, which are the internal limiting membrane (ILM), the Nerve Fiber Layer-Ganglion Cell Complex (NFL-GCC) and the retinal pigment epithelium (RPE). The numerical results are typically plotted on common graphs, and in some cases computed for sectors of a common diagnostic grid, for example, the ETDRS grid. Occasionally statistics are aggregated along a specific criteria to form a normative database. To date such databases have been proprietary to the equipment manufacturer, and the underlying data has not been available for further exploration or exploitation. More commonly, the data only persists long enough to generate a report for a patient file, though an image of the result may be uploaded to an image server for congruity with electronic medical records management.

In general, the existing algorithms used to process this limited data set are imperfect, and the software allows the technician to correct the data on the spot. If the data is not corrected immediately, there is no systematic means for finding, accounting for, or correcting errors in image processing. This problem is exacerbated by advanced multi-layer segmentation algorithms that seek to find more boundaries in soft-tissue structures. Improved methods, systems and computer program products for running multi-layer segmentation algorithms, manually correcting such algorithms on a layer by layer, frame by frame and subject by subject basis are desirable. Furthermore, generally a multi-step process is used to move raw image data from numerical results to statistical tools to diagnosis and clinician or researcher inference. As discussed above, this process is time consuming, expensive, and prone to errors that cannot, in general, be tracked.

Accordingly, some embodiments of the present inventive concept provide methods systems and computer program products that may address these and related problems with collecting, storing, processing, analyzing, reporting and reusing unstructured images and associated metadata for medical imaging in research and clinical settings as will be discussed further herein with respect to FIGS. 1 through 20.

Referring first to FIG. 1, a data processing system 100 in accordance with some embodiments will be discussed. The data processing system 100 may be used to analyze image data acquired by an image acquisition system in accordance with some embodiments of the present inventive concept. As illustrated in FIG. 1, the data processing system 100 may include a user interface 100, including, for example, input device(s) such as a man machine interface (MMI) including, but not limited to a keyboard or keypad and a touch screen; a display; a speaker and/or microphone; and a memory 136 that communicate with a processor 138. The data processing system 100 may further include I/O data port(s) 146 that also communicates with the processor 138. The I/O data ports 146 can be used to transfer information between the data processing system 100 and another computer system or a network, such as an Internet server, using, for example, an Internet Protocol (IP) connection. These components may be conventional components such as those used in many conventional data processing systems, which may be configured to operate as described herein.

Figure 2:
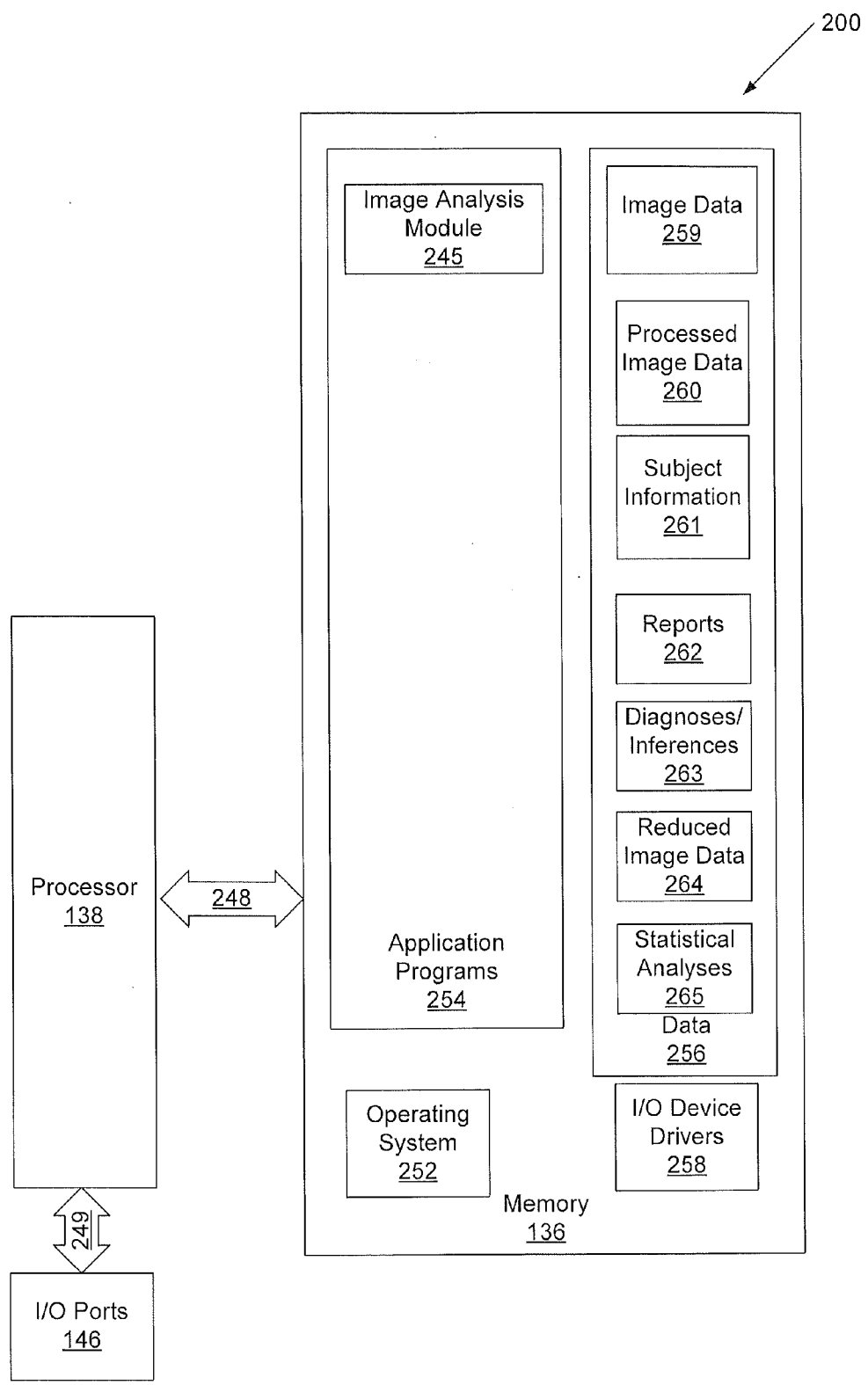
FIG. 2 is a more detailed block diagram of a system according to some embodiments of the present inventive concept.

Referring now to FIG. 2, a more detailed block diagram of the data processing system 100 for implementing systems, methods, and computer program products in accordance with some embodiments of the present inventive concept will now be discussed. It will be understood that the application programs and data discussed with respect to FIG. 2 below may be present in, for example, an image analysis system in accordance with some embodiments without departing from the scope of embodiments discussed herein.

As illustrated in FIG. 2, the processor 138 communicates with the memory 136 via an address/data bus 248 and with the I/O ports 146 via an address/data bus 249. The processor 138 can be any commercially available or custom enterprise, application, personal, pervasive and/or embedded microprocessor, microcontroller, digital signal processor or the like. The memory 136 may include any memory device containing the software and data used to implement the functionality of the data processing system 100. The memory 136 can include, but is not limited to, the following types of devices: ROM, PROM, EPROM, EEPROM, flash memory, SRAM, and DRAM.

As further illustrated in FIG. 2, the memory 136 may include several categories of software and data used in the system 268: an operating system 252; application programs 254; input/output (I/O) device drivers 258; and data 256. As will be appreciated by those of skill in the art, the operating system 252 may be any operating system suitable for use with a data processing system, such as OS/2, AIX or zOS from International Business Machines Corporation, Armonk, N.Y., Windows95, Windows98, Windows2000 or WindowsXP, Windows Vista, Windows7 or Windows CE from Microsoft Corporation, Redmond, Wash., Palm OS, Symbian OS, Cisco IOS, VxWorks, Unix or Linux. The I/O device drivers 258 typically include software routines accessed through the operating system 252 by the application programs 254 to communicate with devices such as the I/O data port(s) 146 and certain memory 136 components. The application programs 254 are illustrative of the programs that implement the various features of the system and may include at least one application that supports operations according to embodiments. Finally, as illustrated, the data 256 may include image data 259, processed image data 260, subject information 261, reports 262, reduced image data 264 derived from processed image data, statistical analyses 265 derived from processed image data and reduced image data, and diagnoses/inferences 263, which may represent the static and dynamic data used by the application programs 254, the operating system 252, the I/O device drivers 258, and other software programs that may reside in the memory 136.

In particular, the image data 259 may include images acquired using an image acquisition system, for example, an OCT system. As discussed above, although some embodiments of the present invention will be discussed herein with respect to Optical Coherence Tomography (OCT) imaging systems, it will be understood that other imaging systems may be used without departing from the scope of the present inventive concept. For example, the images used in the methods, systems and computer program products discussed herein may be acquired using computed tomography (CT) systems, ultrasound systems, magnetic resonance imaging (MRI) systems, positron emission tomography (PET) systems or any other type of imaging system that may be used in combination with one or more of the embodiments discussed herein.

Furthermore, the image data 259 may include acquired images from more than one instrument, and more than one subject or patient. As used herein, "subject" refers to the person or thing being imaged. It will be understood that although embodiments of the present inventive concept are discussed herein with respect to imaging specific portions of an eye of a subject, embodiments of the present inventive concept are not limited to this configuration. The subject can be any subject, including a research animal, a veterinary subject, cadaver sample or human subject and any portion of this subject may be imaged without departing from the scope of the present inventive concept.

Furthermore, although many of the examples discussed herein refer to the sample being an eye, specifically, the retina, cornea, anterior segment and lens of the eye, embodiments of the present inventive concept are not limited to this type of sample. Any type of sample that may be used in conjunction with embodiments discussed herein may be used without departing from the scope of the present inventive concept.

As will be discussed further herein below, using image data 259 associated with more than one subject in accordance with various embodiments of the present inventive concept may provided improved medical data, which may lead to more accurate and swift diagnoses of illnesses and the like.

The processed image data 260 may include the acquired image data 259 after having been processed using various image analysis techniques in accordance with embodiments discussed herein. Again, it will be understood that the processed image data 260 can include processed image data associated with more than one subject. In fact, the more subjects the analysis module in accordance with embodiments discussed herein has access to, the more accurate and refined the results may be.

The subject information data or metadata 261 may include, for example, the subject's name, age, species, gender, ethnicity, and other demographics. This subject information data 261 may also include information related to more than one subject, similar to the image data 259 and the processed image data 260 discussed above.

As will be discussed further below, the output of the image analysis system in accordance with some embodiments may be one of various types of reports 262 as well as various diagnoses/inferences 263 and statistical analyses 265. These reports/diagnoses/inferences may be printed out, stored or provided to a third party application for further processing without departing from the scope of the present inventive concept.

Figure 10:
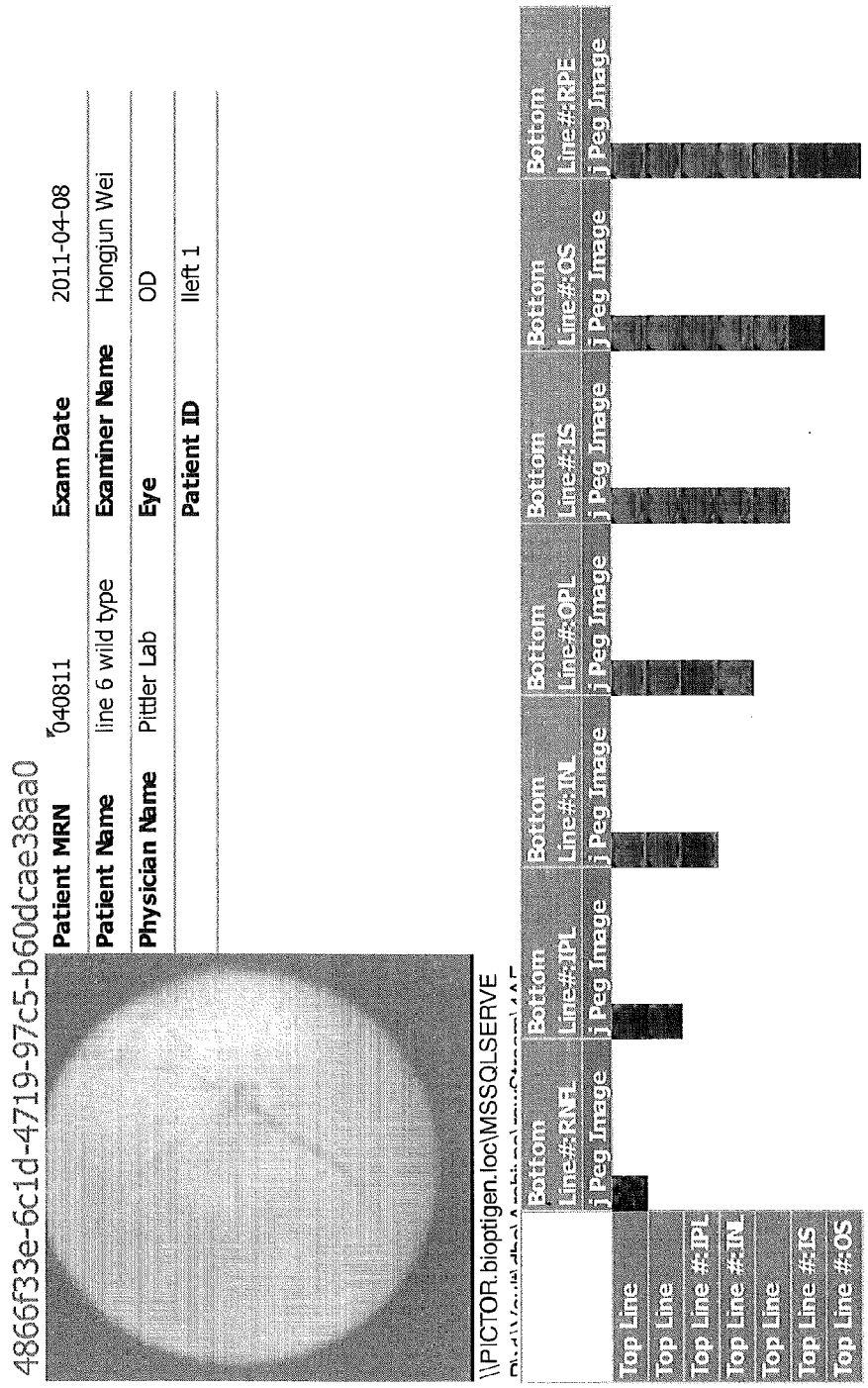
FIG. 10 is a diagram illustrating an exemplary spreadsheet output including heat maps in the cells in accordance with some embodiments of the present inventive concept.
Figure 16:
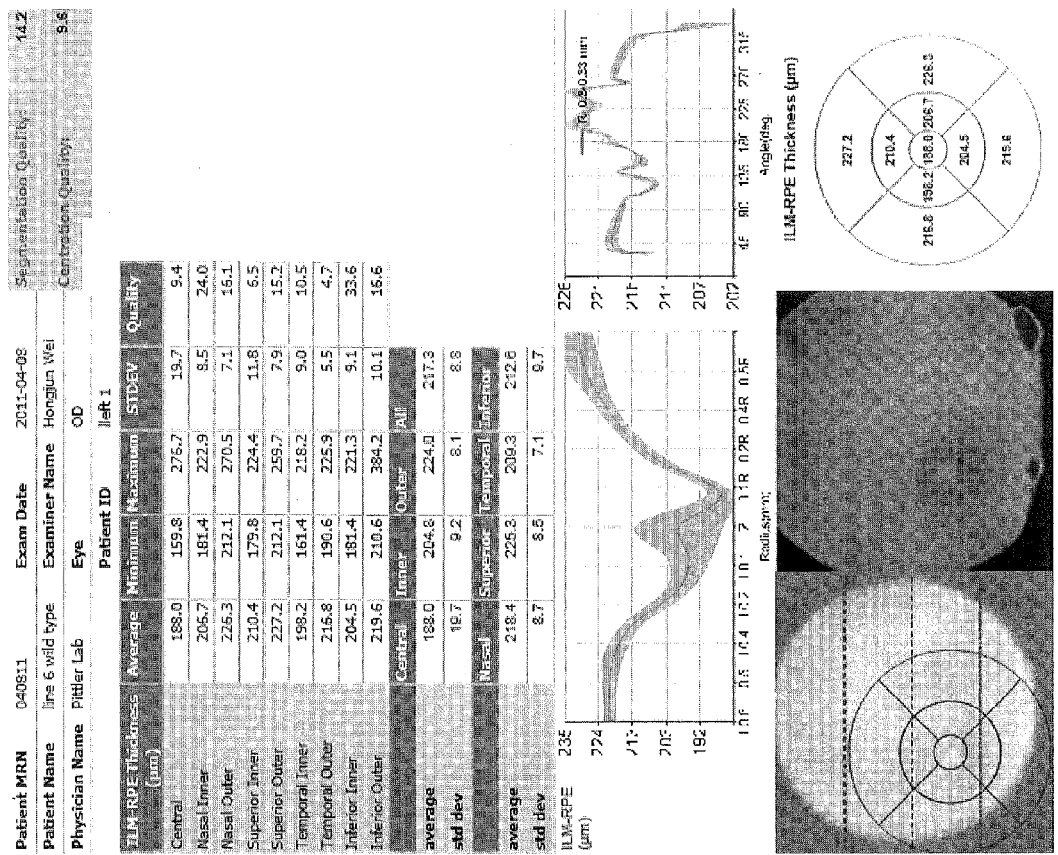
FIG. 16 is a diagram illustrating an exemplary normal report produced using an imaging analysis system in accordance with some embodiments of the present inventive concept.
Figure 17:
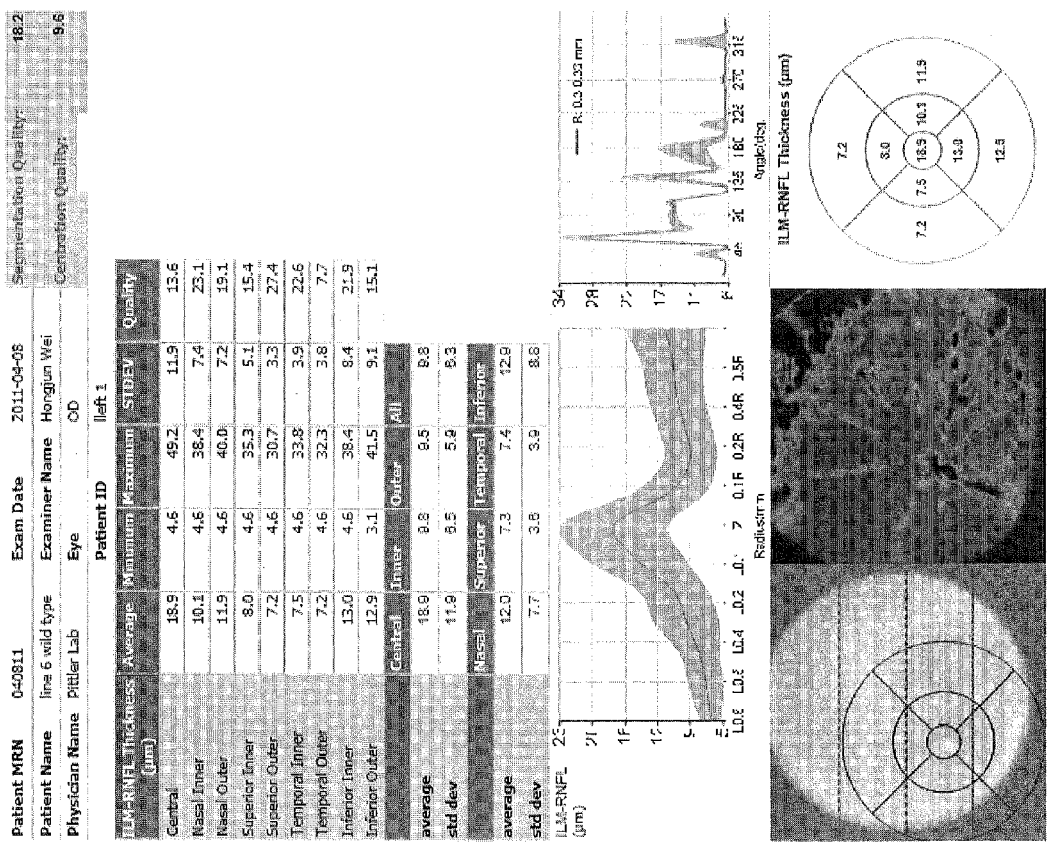
FIG. 17 is a diagram illustrating an exemplary abnormal report produced using an imaging analysis system in accordance with some embodiments of the present inventive concept.
Figure 18:
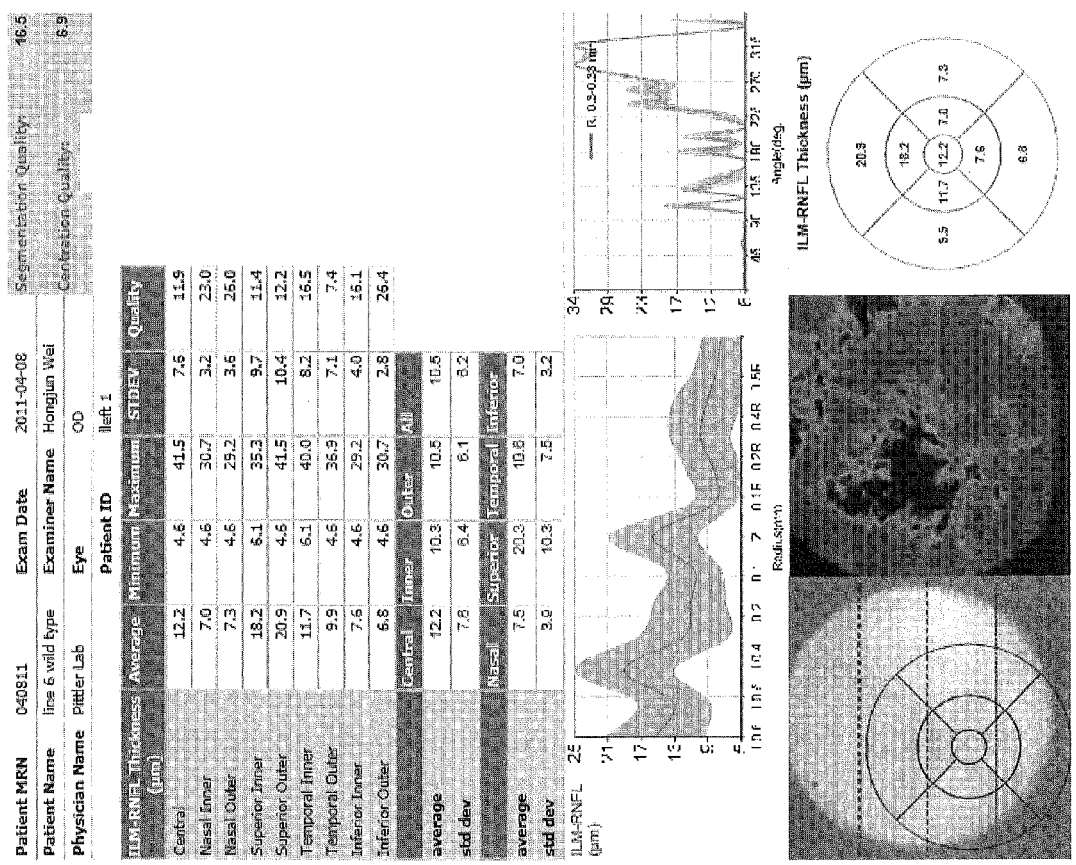
FIG. 18 is a diagram illustrating an exemplary abnormal report produced using an imaging analysis system in accordance with some embodiments of the present inventive concept.
Figure 19:
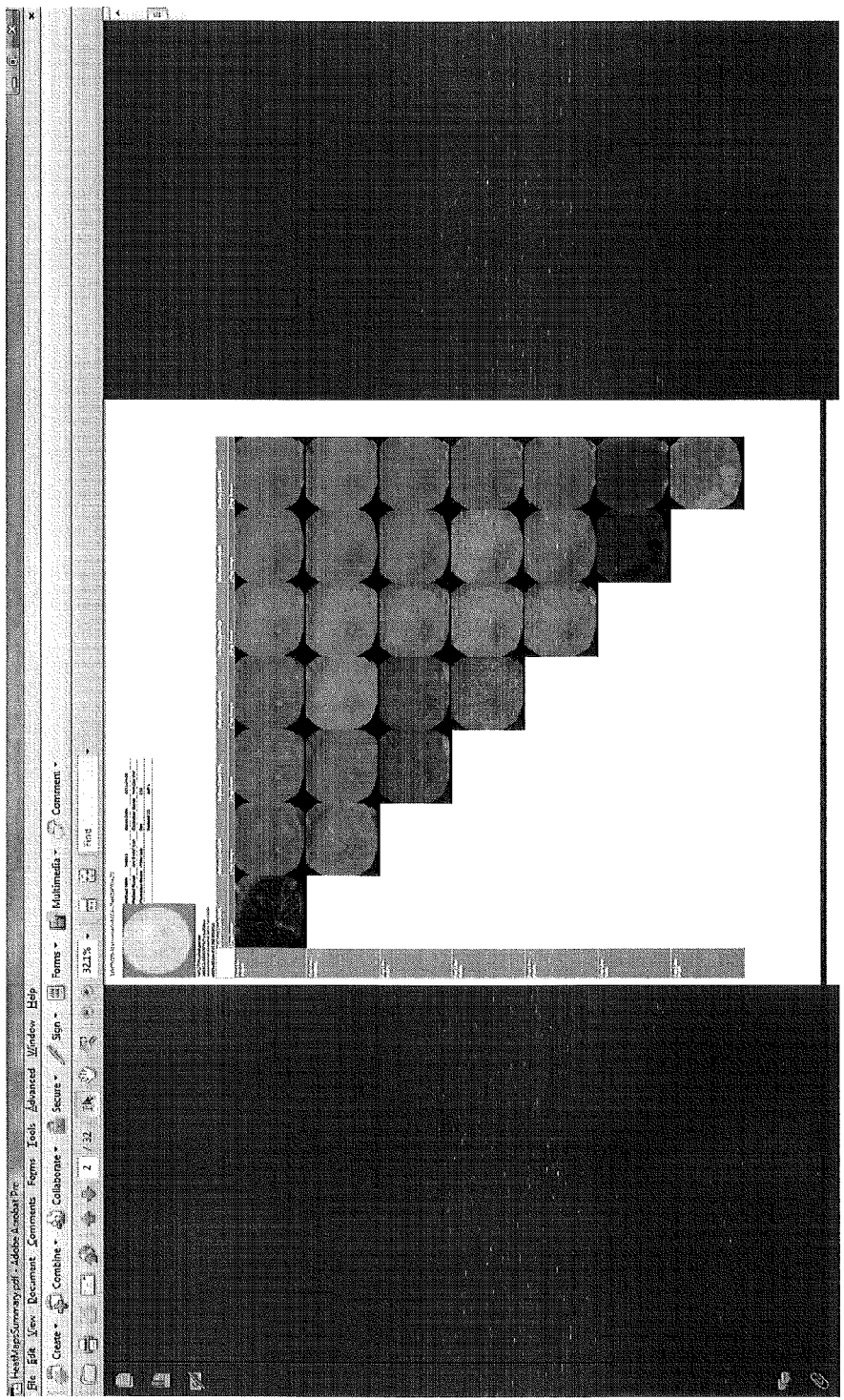
FIG. 19 is a diagram illustrating an exemplary heat map grid produced using an imaging analysis system in accordance with some embodiments of the present inventive concept.

Exemplary reports that may be output from the analysis system in accordance with some embodiments of the present inventive concept will be discussed. For example, FIG. 10 illustrates an exemplary spreadsheet output including heat maps in the cells in accordance with some embodiments of the present inventive concept. FIG. 14 is a diagram illustrating multi-layer segmentation scans produced using an imaging analysis system in accordance with some embodiments of the present inventive concept. FIG. 15 is a diagram illustrating thickness maps produced using an imaging analysis system in accordance with some embodiments of the present inventive concept. FIG. 16 is a diagram illustrating an exemplary normal report produced using an imaging analysis system in accordance with some embodiments of the present inventive concept. FIG. 17 is a diagram illustrating an exemplary abnormal report produced using an imaging analysis system in accordance with some embodiments of the present inventive concept. FIG. 18 is a diagram illustrating an exemplary abnormal report produced using an imaging analysis system in accordance with some embodiments of the present inventive concept. FIG. 19 is a diagram illustrating an exemplary heat map grid produced using an imaging analysis system in accordance with some embodiments of the present inventive concept.

It will be understood that FIGS. 10 and 14-19 are provided as examples only and embodiments of the present inventive concept are not limited in any way by these examples.

As will be appreciated by those of skill in the art, although the data 256 in FIG. 2 is shown as including image data 259, processed image data 260, subject information 261, reports 261 reduced image data 264, statistical analyses 265 and diagnoses/inferences 263, embodiments of the present inventive concept are not limited to this configuration. For example, one or more of these data files may be combined to produce fewer over all files or one or more data files may be split into two or more data files to produce more over all files. Furthermore, completely new data files consistent with embodiments of the present inventive concept may be included in the data 256 without departing from the scope of the present inventive concept.

For example, FIGS. 5 and 6 are charts illustrating various types of data that may be collected, analyzed, shared and the like image analysis systems in accordance with some embodiments of the present inventive concept.

Referring again to FIG. 2, according to some embodiments, the application programs 254 include an image analysis module 245. While the present invention is illustrated with reference to the image analysis module 245, as will be appreciated by those of skill in the art, other configurations fall within the scope of embodiments discussed herein. For example, rather than being an application program 254, these circuits or modules may also be incorporated into the operating system 252 or other such logical division of the system. Furthermore, while the image analysis module 245 is illustrated in a single system, as will be appreciated by those of skill in the art, such functionality may be distributed across one or more systems. Thus, the embodiments discussed herein should not be construed as limited to the configuration illustrated in FIG. 2, but may be provided by other arrangements and/or divisions of functions between data processing systems. For example, although FIG. 2 is illustrated as having only a single module, this module may be split into two or more circuits/modules without departing from the scope of embodiments discussed herein.

Figure 3:
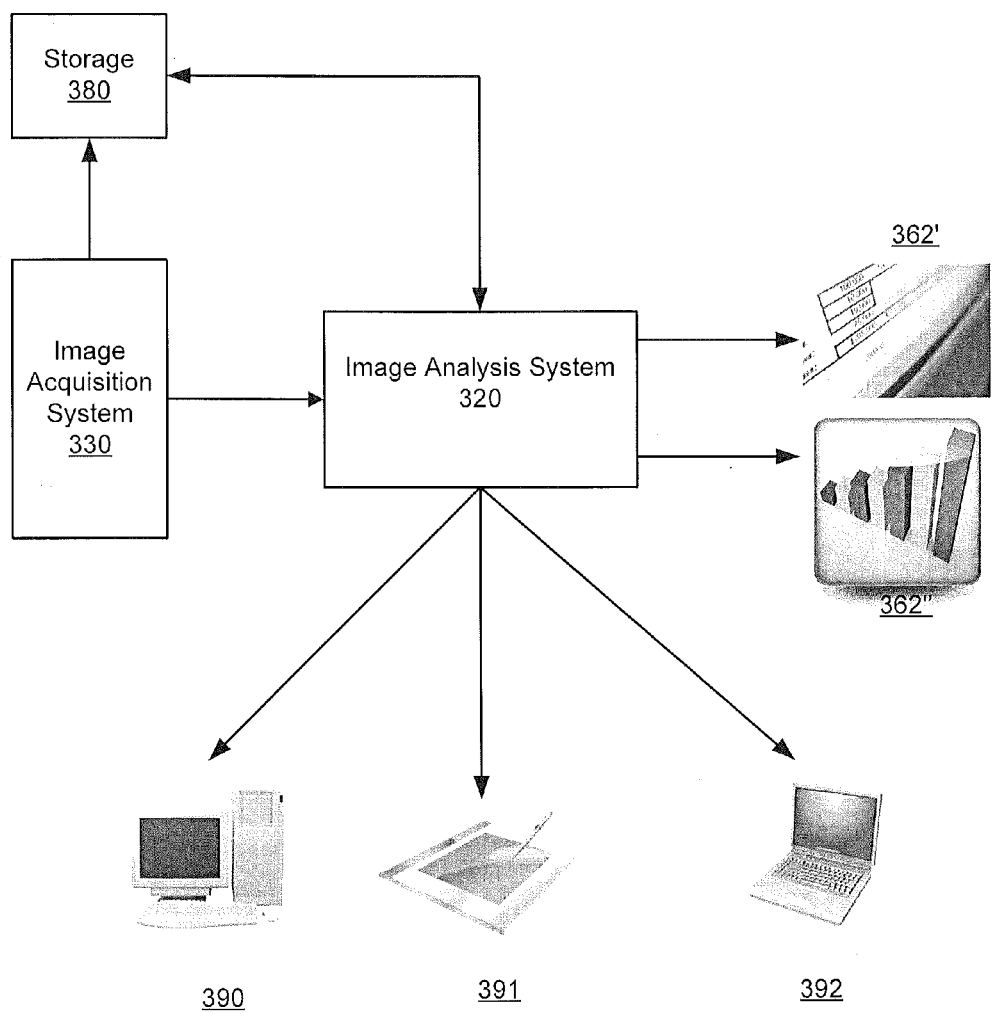
FIG. 3 is a block diagram illustrating a system including an Image Analysis System in accordance with some embodiments of the present inventive concept.

The image analysis module 245 is configured to process received image data in accordance with embodiments discussed herein. FIG. 3 is a block diagram illustrating a system including an image analysis system 320 in accordance with some embodiments of the present inventive concept. The data processing system and the image analysis module 245 discussed with respect to FIGS. 1 and 2 can be included in the image analysis system 320 of FIG. 3.

Referring now to FIG. 3, a system in accordance with some embodiments may include an imaging system 330, at least one external storage device 380, an image analysis system 320 in accordance with embodiments discussed herein, one or more third party systems 390, 391 and 392 and outputs of the system 362' and 362" (reports). As discussed above, the image acquisition system 330 may be an OCT system or any other type of imaging system capable of providing images that can be used in accordance with embodiments discussed herein.

The storage device 380 can be one or more storage devices. It may be external storage or local storage, i.e. incorporated into the image acquisition system 320 or the image analysis system 320, without departing from the scope of the present inventive concept.

The third party communications devices 390, 391, 392 may be, for example, a desktop computer 390, a tablet 391 or a lap top computer without departing from the scope of the present inventive concept. The communications device can be any type of communications device capable of communicating with the image analysis system 320 over a wired or wireless connection. Although only three communication devices are illustrated in FIG. 3, embodiments are not limited to this configuration. For example, more or less than three communication devices may be present without departing from the scope of embodiments discussed herein.

If the communications device is a portable electronic device, as used herein "portable electronic device" includes: a cellular radiotelephone with or without a multi-line display; a Personal Communications System (PCS) terminal that combines a cellular radiotelephone with data processing, facsimile and data communications capabilities; a Personal Data Assistant (PDA) that includes a radiotelephone, pager, Internet/intranet access, Web browser, organizer, calendar and/or a global positioning system (GPS) receiver; a gaming device, an audio video player, and a conventional laptop and/or palmtop portable computer that includes a radiotelephone transceiver.

The reports 362' and 362" may include the same or similar information discussed above with respect the reports 262 and diagnoses/inferences 263 discussed above with respect to FIG. 2 and the outputs illustrated in FIGS. 10 and 14-19.

FIG. 4 illustrates the system of FIG. 3 with various picture diagrams. Like references numerals refer to like elements throughout. Thus, details with respect to the elements illustrated in FIG. 4 will not be repeated herein in the interest of brevity.

Figure 7:
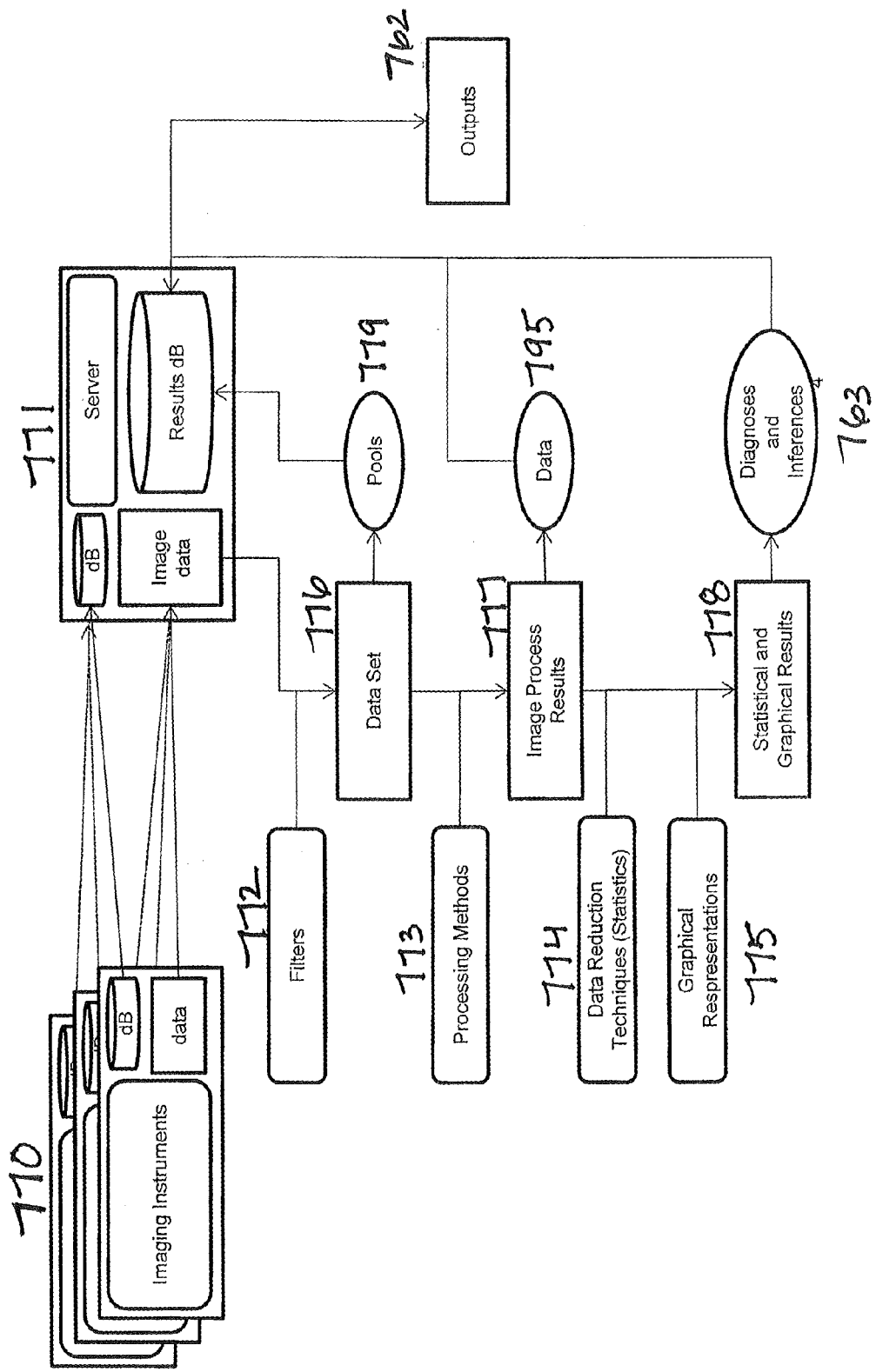
FIG. 7 is a flow chart illustrating operations in accordance with some embodiments of the present inventive concept.

FIG. 7 is a flow diagram illustrating operations in accordance with some embodiments of the present inventive concept. Referring now to FIGS. 3, 4 and 7, operations of the system of FIGS. 3 and 4 will be discussed with reference to the flow diagram of FIG. 7. One or more imaging instruments 770 of the image acquisition system 330, 430 may be used to acquire image(s) from one or more subjects. These acquired images may be stored at the image acquisition system 330, 430, externally 380, 480 or anywhere that may be accessible to the image analysis system 320, 420. FIG. 7 illustrates an external database 771 (380, 480), which may be combined with other modules/devices as discussed above.

Figure 8:
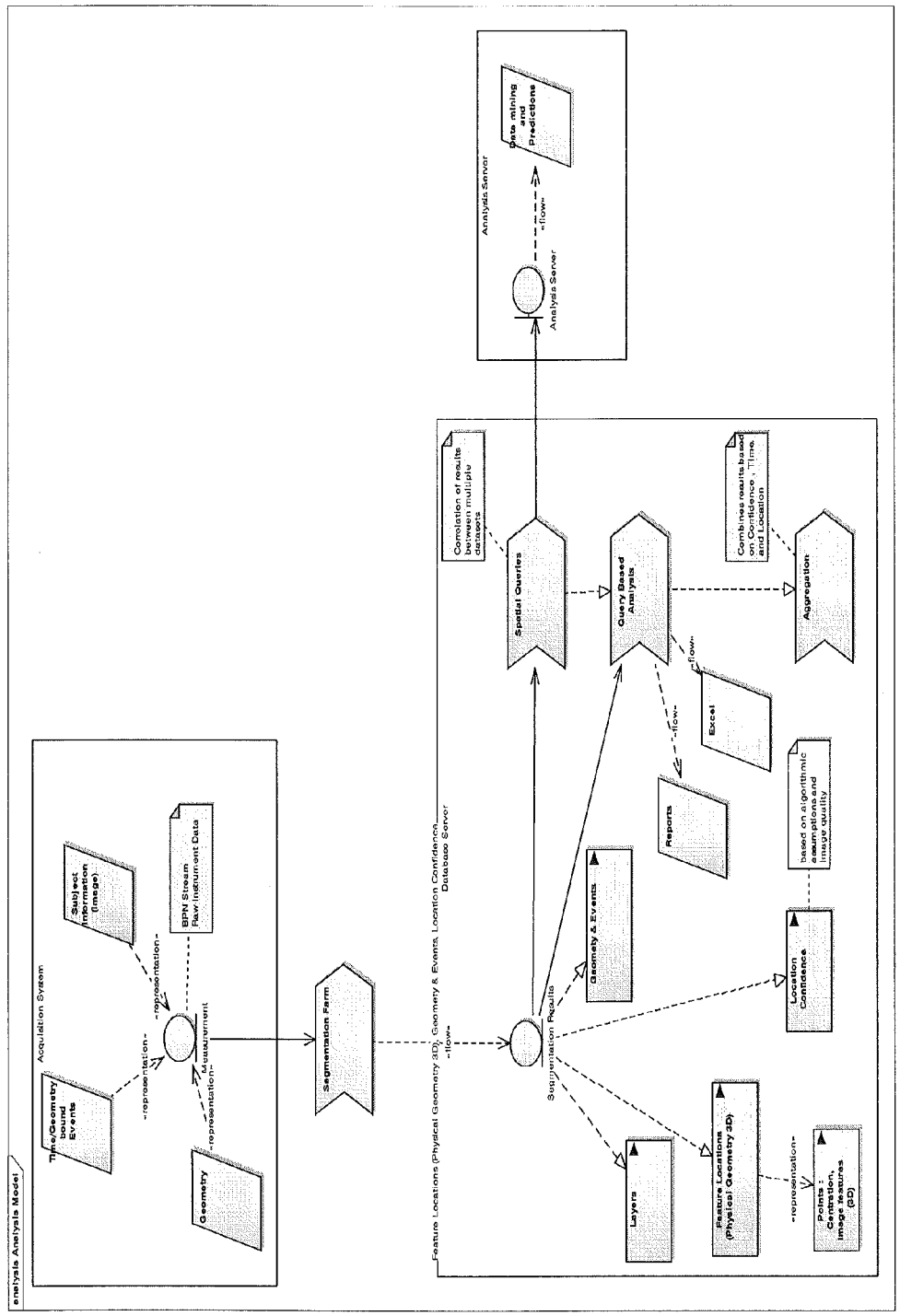
FIG. 8 is a block diagram illustrating exemplary architecture of the image analysis system in accordance with some embodiments of the present inventive concept.

Before the stored images are processed in accordance with embodiments discussed herein, filters 772 for selecting a subset of available images from the complete set of available raw images or previously processed data based on available metadata, methods for processing 773 the raw acquired images or processed data may be selected, and statistical methods 774 for analyzing the acquired and processed data, graphical representations 775 may be selected. All of these selections may be made prior to processing the image(s) such that the processing methods proceed automatically without user intervention. The data set 776, the image process results 777, the statistical and graphical results 778 can all be both inputs and outputs of the systems such that the system continually refines the data to provide more meaningful data. As discussed above and further below, the data 795 may be pooled 779 to provide diagnoses/interferences 763 (263) and outputs 762 (262) and further refine the same. FIG. 8 is a block diagram illustrating one exemplary architecture of the image analysis system in accordance with some embodiments of the present inventive concept.

Various details and embodiments of the image analysis system will now be discussed. However, embodiments of the present inventive concept should not be limited in any way by the following details. Some embodiments of the present inventive concept may reduce the burden of manual image correction associated with automated algorithm image processing methodologies such as segmentation of retinal layers in optical coherence tomography images. Some embodiments of the present inventive concept include a computer system for automated image processing such as retinal layer segmentation and at least two methods for improving the accuracy of the automated image processing results for downstream analysis. Methods in accordance with some embodiment include statistical aggregation of data and excluding outliers that exceed a threshold with respect to a measure of statistical distribution, such as excluding data that is greater than 3 standard deviations from a mean.

Some embodiments of the present inventive concept may facilitate pooling images for analysis based on filtering available metadata associated with the images. The image metadata may include one or more of: a patient demographic data; an individual responsible for drawing inferences from the data; an individual responsible for acquiring the images; a window of time for acquiring the images; a position in a sequence of events along which images may be acquired; a descriptor of instruments that may be used to acquire the image data; a descriptor of instrument settings used to acquire an image; a descriptor of image quality associated with an image; quantitative results derived from the image; an inference applied to the image; and an annotation associated with an image. Descriptors in accordance with some embodiments include a quantitative metric associated with a quality of all or part of an image. A descriptor may include a signal-to-noise ratio of the image, an average noise of the image, a noise variance of the image, a measure of image distortion, an attribute histogram, or a texture map.

Methods in accordance with some embodiments include identifying a boundary or a layer or an area or a volume within an image. Methods may also include computing a flow within a region, such as through the application of Doppler flow computation techniques known in the art, or the application of annotations to a point or region of an image.

The primary results obtained by a first application of one or more methods may be processed according a second set of methods to obtain a reduced set of results. The reduced set of results may include a computation of distances between boundaries, layers or other results obtained by application of a first set of methods. The reduced set of results may include the aggregation of primary results or other reduced results in a a statistical summarization of all or a partial set of such results. For example, a reduced set of results may include the count of image pixels or voxels within a sector of an image, the average value of the distance between one or more pairs of boundary layers across the sector, the variance or standard deviation of this set of distances, and any higher order statistical moment of these value, for example to assess the skew or kurtosis of the distribution, or the confidence level for assessing the mean of the values.

Methods in accordance with some embodiments include applying a confidence map with correspondence to the data, the confidence map expressing a degree of goodness of the performance of the algorithm. The degree of "goodness" may be derived by assessing a rate of change between neighbors of data points, with decreasing confidence associated with rates of change exceeding given criteria. Other criteria may include information returned from the algorithm on the other criteria used directly by the algorithm. The statistical data and/or the confidence maps may be used to fully exclude poor data, or to fill in poor data by obtaining weighted averages of neighboring data points, the weights derived by the statistical strength or confidence levels of the applied data points.

Figure 9:
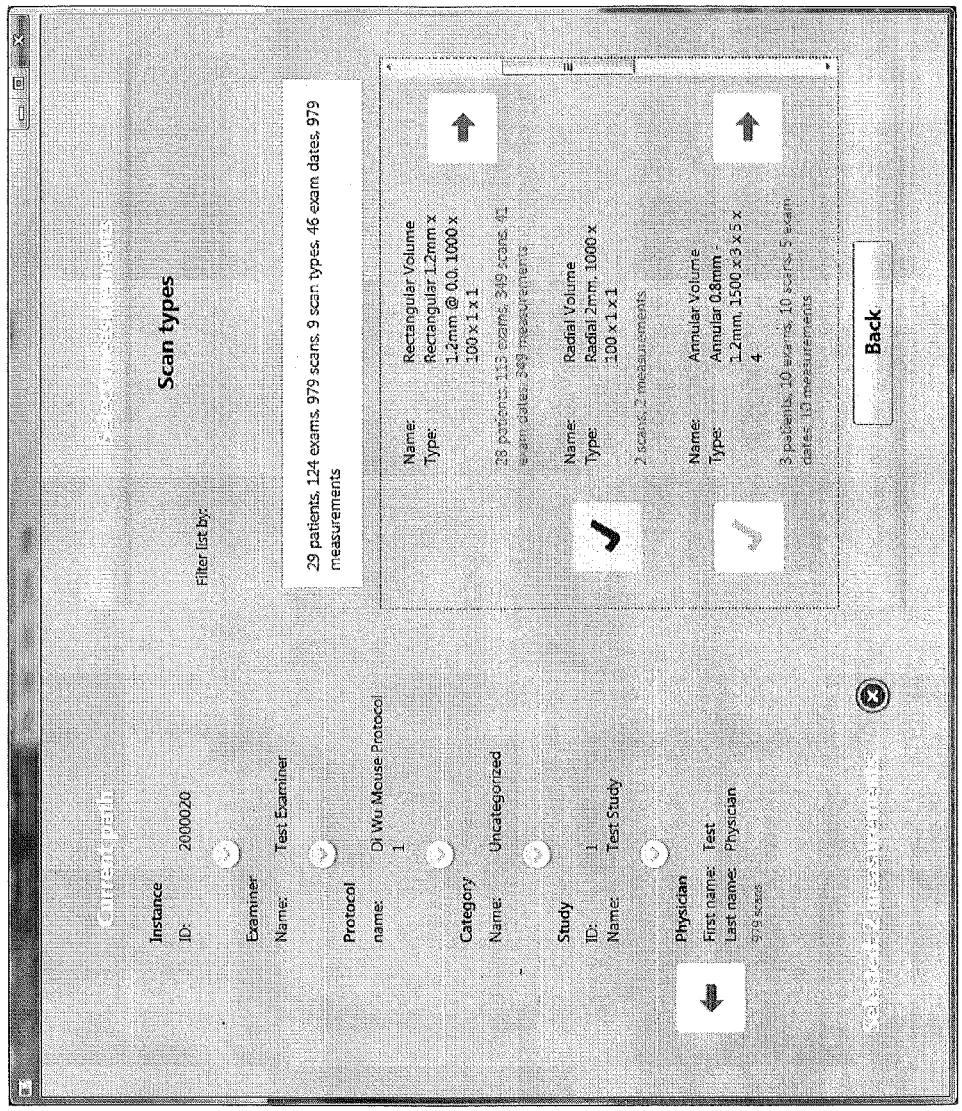
FIG. 9 is a graphical user interface illustrating a metadata hypercube browser and filter in accordance with some embodiments of the present inventive concept.

Some embodiments of the present inventive concept may facilitate the pooling of data from multiple subjects for systematic analysis along multiple dimensions of inquiry. Some embodiments of the present inventive concept include a database to store metadata that contains state information about the subject (name, age, species, gender, ethnicity, other demographics, etc.) and a database to store results of processed images as discussed above with respect to FIG. 2. The results database effectively turns the unstructured raw images into a structured set of results. A multidimensional query (hypercube) may allow the researcher to search both databases for correlated sets of information along as many filters as there are fields in the metadata and results data base to create pooled data sets with a well defined set of relationships. An exemplary graphical user interface illustrating an embodiment of the hypercube is illustrated in FIG. 9.

Some embodiments of the present inventive concept may be used to validate research methodology. A research methodology may include, for example, algorithmic methods to process data to extract results; the evaluation of model subjects, for example with specific hypothesized disease proclivities; or particular paths to treatment. The image analysis system discussed herein may allow processing of same data pools on multiple algorithms, generating and storing processing results including statistical information and confidence information, and the processing statistical tests such as analysis-of-variance (ANOVA) on the multiple pools of method-specific results to assess performance differences between the methods. Similarly, multiple pools from populations of subjects and/or treatments may be processed and tested against one or multiple image processing methodologies, and hypothesis tested using statistical methods applied to the resultant data.

Some embodiments of the present inventive concept provide that the processed results are suitably structured for direct transfer to third-party statistical analysis packages as discussed above.

Some embodiments of the present inventive concept may provide prospective research design if facilitated by the system. Embodiments discussed herein may allow the definition of studies, subject populations, treatment arms representing aspects of the study, and end points for analysis. For example, the study may involve the assessment of treatments for retinitis pimentosa; the subjects may include a wild type mouse model and a retinitis pigmentosa mouse model; the treatments arms may include a pharmaceutical therapy and a genetic therapy; the endpoints may include total retinal thickness over time, outer nuclear layer thickness over time, ratio of inner nuclear layer to outer nuclear layer over time. Furthermore, the algorithms for obtaining the end point data may be in flux. Thus, embodiments discussed herein may allow for a priori definition of these and other classes of the experiment. As data is acquired and processed, results are collected and tagged with appropriate metadata, and pooled results analyzed along any or all dimensions of the study, and statistical methods applied to the results. All of this functionality may be accomplished on a single system, after data acquisition, with minimal manual intervention required beyond selecting filters for pooling data, methods for processing data, and statistical methods for analyzing data. Furthermore, the steps of selecting filters, processing methods and statistical approaches may be defined a prior, and the results automatically processed through to output on available data meeting the criteria. Further still, the processing may be run at anytime within the study, and rerun at any time in the study, for example as more data is made available. Furthermore, the pools may be changed by eliminating certain data sets according to new filters, re-running with new analysis algorithms, or re-running against new statistical tests for an original or modified hypothesis.

Some embodiments of the present inventive concept facilitate designed experiments, for example, Taguchi experiments, allowing the definition of multi-factor, multi-level experiments, reducing the full factorial design to a reduced design, specifying the factors and levels to be tested according to the design, tagging experimental results with their particular role in the design, automating the image processing per some embodiments of the present inventive concept, and automatically generating the statistical results, for example, an ANOVA to assess the relative impact of the various factors. In some embodiments of the present inventive concept multiple endpoints (algorithms) may be attached to the experiment, and further that the experiment can be re-processed on existing data with new end-points or improved or modified methods.

Some embodiments of the present inventive concept may enable longitudinal (time series) analysis of data on individual subjects or pooled subjects. A key problem in longitudinal studies involving images is to return to the same location in an image at sequential periods in time. Thus, some embodiments of the present inventive concept provide a map of the subject based on one or more landmarks, and to compare longitudinal data on a point in subsequent images with reference to the map. The comparison may be on a point, a weighted average of data in the neighborhood of the point, or a sector of more extended area defined with respect to the landmark. Example landmarks for a retina may include, for example, a fovea, and optic nerve head, or a branch point of major blood vessels.

In some embodiments of the present inventive concept the system automatically identifies one or more landmarks and that further, if image magnification or orientation changes, the system automatically uses two or more landmarks to assess magnification and rotation. The landmarks may be defined in multiple ways, including for example: by user annotation, automatically identified by definable volumetric points, automatically defined by projects of the volume to a planar image, or by using the processed data to find, for example, peak or minimum values in a particular attribute, such as thickness.

Some embodiments of the present inventive concept may further increase the structure of the experimental data in a manner readily accessible by the researcher for subsequent analysis, data reduction and reporting. Some methods for thus improving the management of such data sets is through publication of processed results to structured outputs, including DICOM files, spreadsheets, and other third-party analysis tools. As an example single sample data may output to a multi-tab spreadsheet. Each tab may contain results of processed data by frame of a volume image. Within each tab, an image of the original frame may reside in a cell. The image may include a graphical overlay of the layers identified in the image processing step. Additional cells may define a matrix with each layer boundary occupying a row position and a column position, and the intersecting cell containing a value pertaining to a resultant value obtained between the segments of defined by the row and column. The values may be layer thicknesses or other attribute. When filled, the matrix may be an upper triangular matrix holding values for a relationship such as thickness between each boundary identified during processing. The spreadsheet is structured regularly such that cell positions and value types are constant across the sheet, enabling simple cross-tab or cross sheet operations for subsequent data reduction by technicians with only rudimentary knowledge of spreadsheets. A spreadsheet may further contain the results of pooled data, where the corresponding values are statistical values including but not limited to means and variances. The spreadsheets may be further organized such that the various tabs reflect sectors as defined by a landmarked grid, rather than specific frames of the images.

Some embodiments of the present inventive concept publish graphical results to the spreadsheets in addition to or instead of numerical data results. For example, instead of layer thickness, a graphical "heat map" or colored thickness map may be output to the respect cells. Another graphical representation for output to cells is segmented projections of the original volumetric image data. For example, intensity projections bounded by the algorithmically identified layers may be recorded into the cells. The intensity projections may be, without limitation, average intensity projections, median value projections, or maximum value projections. The use of numerical data combined with such graphical information automatically compiled into such structured organizations will greatly facilitate the combined quantitative and qualitative assessment of complex experimental results.

Some embodiments of the present inventive concept increase the reuse of image data. All available data may be reprocessed as described using new or revised image processing or data reduction methods, and results from processing method may be compared against results from another methods. Further, the processed results from a first algorithmic method may form the inputs to a second method. As an example, a first method may derive the boundaries for layers of a retina. A subsequent method may count the number of blood vessels identifiable within each layer, or obtain a histogram distribution of scattering intensities within each layer, or count features within a range of sizes within each layer.

Some embodiments of the present inventive concept may increase or possibly maximize reuse of expensive clinical data bay allowing mining of data using filters of original metadata, using filters of results derived during processing steps, using diagnostic conclusions or inferences recorded after processing. After mining, the resultant data pools may be processed using new methods, including methods not foreseen during the design of the original experiment. Such applications will facilitate retrospective studies applying new hypotheses and new processing methodologies and new data reduction techniques to existing data sets.

Some embodiments of the present inventive concept may facilitate collaboration among researchers using shared data sets, filters, image processing techniques, data reduction techniques, and reporting techniques. Some embodiments of the present inventive concept include local data servers and remote internet based (cloud) data servers, and the remote data servers may be single point or distributed. The interface to the processing server may be through a web services interface allowing multiple users to access data simultaneously. The system may allow multiple sites with multiple image capture devices to upload data for independent or multi-site experiments; metadata may include unique information tying data to the particular instrument from which the raw data is captured. Users may upload new methods, including image processing and data reduction methods, and such methods may be open for general use or proprietary with controlled usage rules. Further, to maintain patient confidentiality in clinical trials, patient identifying data may be encrypted with a key maintained by the particular originator of particular data sets.

Figure 11:
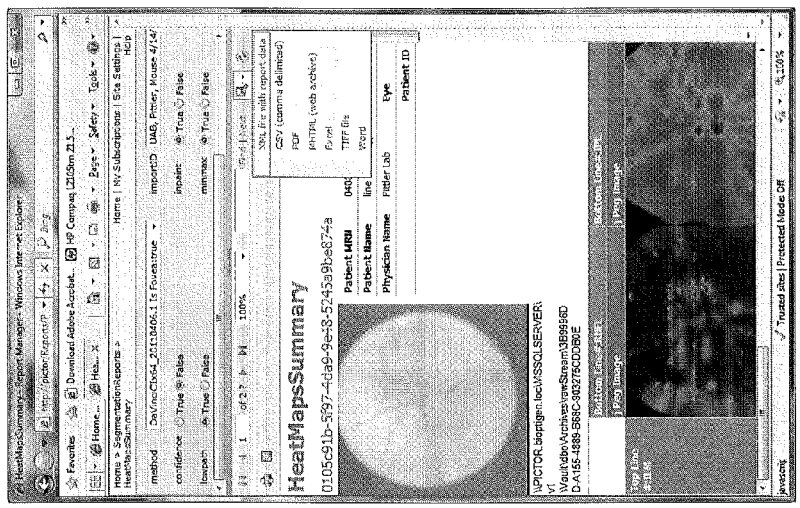
FIG. 11 is a graphical user interface illustrating an exemplary web services interface in accordance with some embodiments of the present inventive concept.
Figure 12:
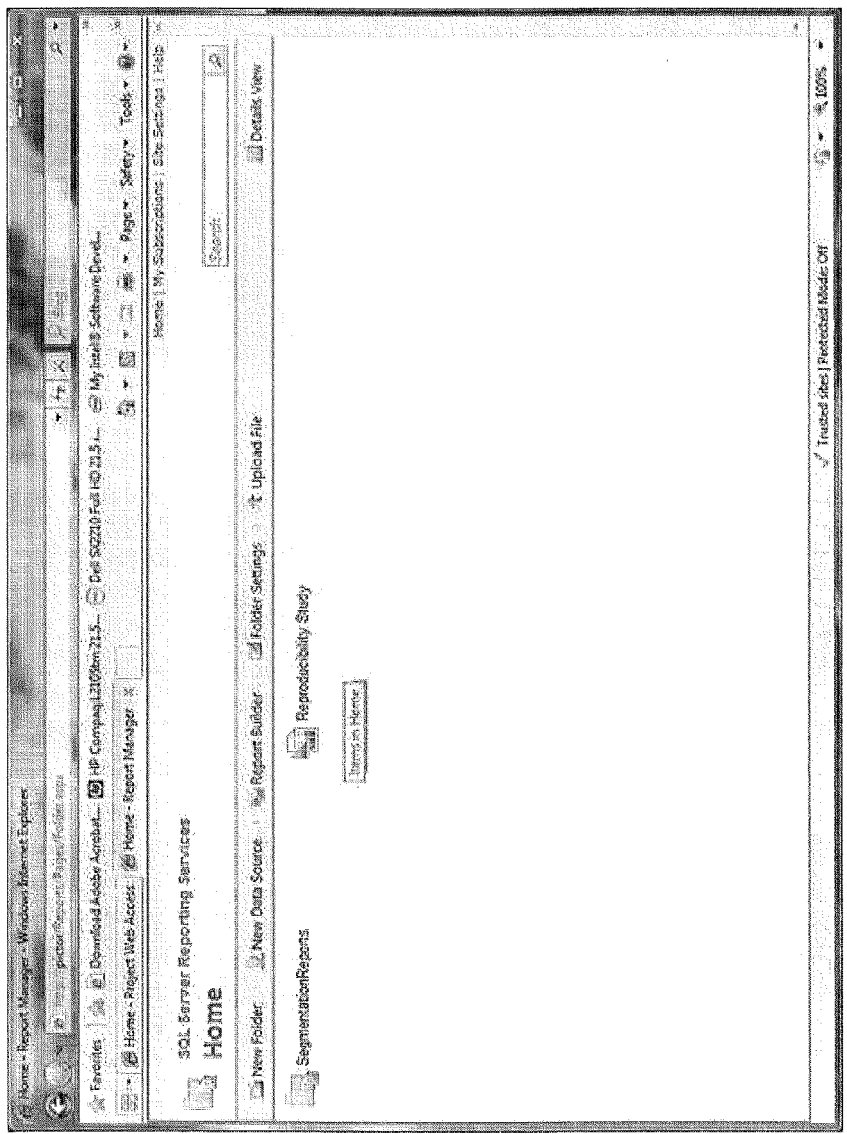
FIG. 12 is a graphical user interface illustrating an exemplary web services reporting interface in accordance with some embodiments of the present inventive concept.
Figure 13:
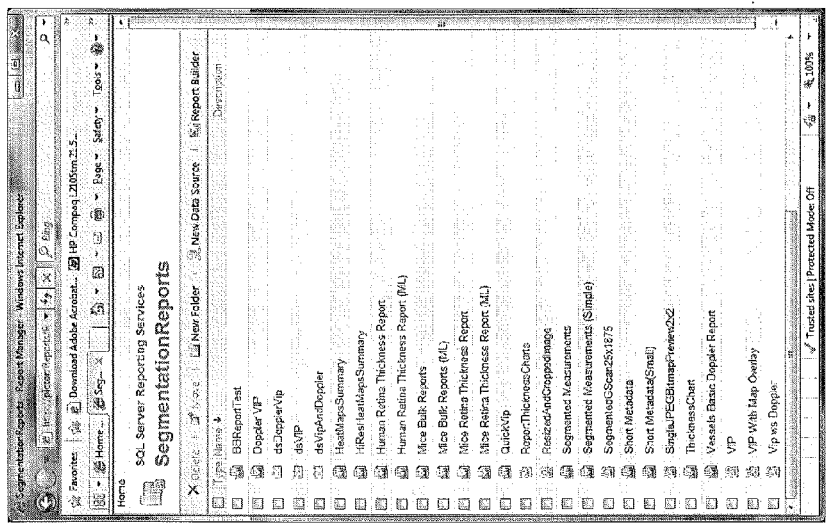
FIG. 13 is a graphical user interface illustrating an exemplary web services reports browser in accordance with some embodiments of the present inventive concept.

Various aspects of the present inventive concept discussed above are illustrated in the Figures. For example, FIG. 11 illustrates a graphical user interface of an exemplary web services interface in accordance with some embodiments of the present inventive concept. FIG. 12 illustrates a graphical user interface of an exemplary web services reporting interface in accordance with some embodiments of the present inventive concept. FIG. 13 illustrates a graphical user interface an exemplary web services reports browser in accordance with some embodiments of the present inventive concept.

Figure 20:
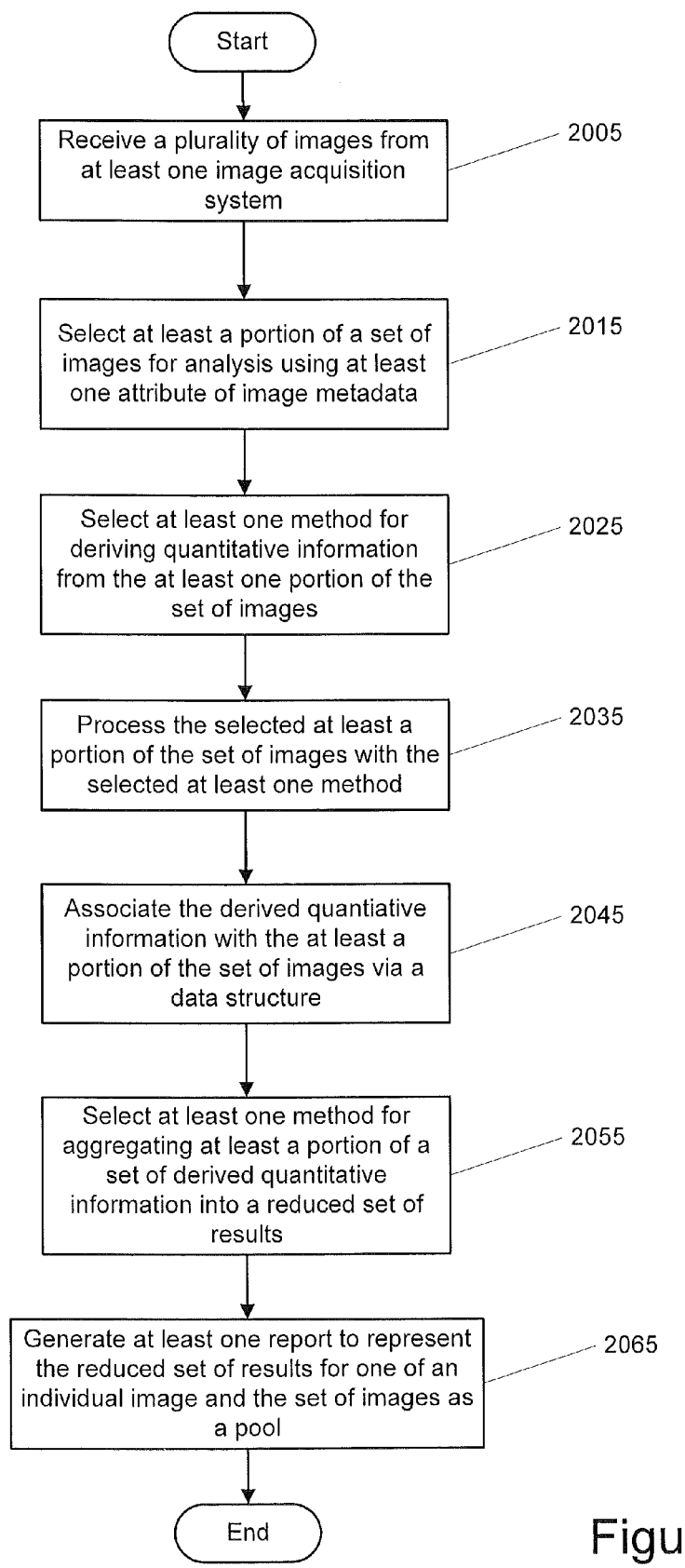
FIG. 20 is a flowchart illustrating operations in accordance with various embodiments of the present inventive concept.

Referring now to FIG. 20, operations according to various embodiments of the present inventive concept will now be discussed. Operations for analyzing images acquired using an image acquisition system being at block 2005 by receiving a plurality of images from at least one image acquisition system (block 2005). Operations continue by selecting at least a portion of a set of images for analysis using at least one attribute of image metadata (block 2015); selecting at least one method for deriving quantitative information from the at least a portion of the set of images (block 2025); processing the selected at least a portion of the set of images with the selected at least one method for deriving quantitative information (block 2035); associating the derived quantitative information with the at least a portion of the set of images via a data structure (block 2045); selecting at least one method for aggregating at least a portion of a set of derived quantitative information into a reduced set of results (block 2055); and generating at least one report to represent the reduced set of results for one of an individual image and the set of images as a pool (block 2065).

In some embodiments, the at least one images acquisition system may be at least one Optical Coherence Tomography (OCT) imaging system. In certain embodiments, the at least one OCT imaging system may be at least one Fourier Domain Optical Coherence Tomography imaging System.

The image metadata may include one or more of: a patient demographic data; an individual responsible for drawing inferences from the data; an individual responsible for acquiring the images; a window of time for acquiring the images; a position in a sequence of events along which images may be acquired; a descriptor of instruments that may be used to acquire the image data; a descriptor of instrument settings used to acquire an image; a descriptor of image quality associated with an image; quantitative results derived from the image; an inference applied to the image; and an annotation associated with an image.

The method may further include one or more of a marking, a structural measurement, a functional measurement, a descriptor, and an annotation. The method may include one of a method involving user intervention with a representation of the image displayed on graphical display; a method that is fully automated through computer algorithms without user intervention; and a method including a combination of user intervention and computer algorithms.

A boundary of a layer, an area or a volume may be identified within the structure of the image. In some embodiments, one or more regions of relative motion within the structure of the image may be identified.

The method may further include computing a flow within a region represented by the image. A descriptor of a portion of an image may be computed. The descriptor may be one or more of a signal-to-noise ratio, an average noise, a noise variance, a distortion, an attribute histogram and a texture map.

The reduced set of results may include a measurement of distances between boundaries identified within the structure of an image. The data structure may include one or more of a database, a file structure, and a spreadsheet.

The reduced set of results may include a statistical summarization of the measurement data according to a sector map defined for the image. In certain embodiments, the statistical summarization may include one or more of a count, an average, a variance, a standard deviation, and a higher order moment. The statistical summarization may include the computation of a confidence interval for the reduced results.

The report may be derived from pooled statistical results from more than one image drawn from the image set. The sector map may include one or more of a regular grid, a volumetric matrix, and a defined grid associated with a clinical or other standard.

In some embodiments, the report may include one or more of a data table; a two dimensional projection of volumetric data onto a plane; heat map that associates a color or a gray-scale map to a two dimensional projection of reduced data values onto a plane; a spreadsheet of values derived from the image; and a spreadsheet of reduced values derived from image.

In further embodiments, the at least one image acquisition system may include at least one Fourier Domain Optical Coherence Tomography imaging System and wherein the Fourier Domain Optical Coherence Tomography images are images of a region of an eye.

The region of the eye may be selected from one of an anterior segment, cornea, a sclera, a crystalline lens, an iris, an iridocorneal angle, an implanted intraocular lens, a posterior segment, a retina, a macula, an optic nerve head, and a peripheral retina.

Example embodiments are described above with reference to block diagrams and/or flowchart illustrations of methods, devices, systems and/or computer program products. It is understood that a block of the block diagrams and/or flowchart illustrations, and combinations of blocks in the block diagrams and/or flowchart illustrations, can be implemented by computer program instructions. These computer program instructions may be provided to a processor of a general purpose computer, special purpose computer, and/or other programmable data processing apparatus to produce a machine, such that the instructions, which execute via the processor of the computer and/or other programmable data processing apparatus, create means (functionality) and/or structure for implementing the functions/acts specified in the block diagrams and/or flowchart block or blocks.

These computer program instructions may also be stored in a computer-readable memory that can direct a computer or other programmable data processing apparatus to function in a particular manner, such that the instructions stored in the computer-readable memory produce an article of manufacture including instructions which implement the functions/acts specified in the block diagrams and/or flowchart block or blocks.

The computer program instructions may also be loaded onto a computer or other programmable data processing apparatus to cause a series of operational steps to be performed on the computer or other programmable apparatus to produce a computer-implemented process such that the instructions which execute on the computer or other programmable apparatus provide steps for implementing the functions/acts specified in the block diagrams and/or flowchart block or blocks.

Accordingly, example embodiments may be implemented in hardware and/or in software (including firmware, resident software, micro-code, etc.). Furthermore, example embodiments may take the form of a computer program product on a computer-usable or computer-readable storage medium having computer-usable or computer-readable program code embodied in the medium for use by or in connection with an instruction execution system. In the context of this document, a computer-usable or computer-readable medium may be any medium that can contain, store, communicate, propagate, or transport the program for use by or in connection with the instruction execution system, apparatus, or device.

The computer-usable or computer-readable medium may be, for example but not limited to, an electronic, magnetic, optical, electromagnetic, infrared, or semiconductor system, apparatus, device, or propagation medium. More specific examples (a non-exhaustive list) of the computer-readable medium would include the following: an electrical connection having one or more wires, a portable computer diskette, a random access memory (RAM), a read-only memory (ROM), an erasable programmable read-only memory (EPROM or Flash memory), an optical fiber, and a portable compact disc read-only memory (CD-ROM). Note that the computer-usable or computer-readable medium could even be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory.

Computer program code for carrying out operations of data processing systems discussed herein may be written in a high-level programming language, such as Java, AJAX (Asynchronous JavaScript), C, and/or C++, for development convenience. In addition, computer program code for carrying out operations of example embodiments may also be written in other programming languages, such as, but not limited to, interpreted languages. Some modules or routines may be written in assembly language or even micro-code to enhance performance and/or memory usage. However, embodiments are not limited to a particular programming language. It will be further appreciated that the functionality of any or all of the program modules may also be implemented using discrete hardware components, one or more application specific integrated circuits (ASICs), or a field programmable gate array (FPGA), or a programmed digital signal processor, a programmed logic controller (PLC), or microcontroller.

It should also be noted that in some alternate implementations, the functions/acts noted in the blocks may occur out of the order noted in the flowcharts. For example, two blocks shown in succession may in fact be executed substantially concurrently or the blocks may sometimes be executed in the reverse order, depending upon the functionality/acts involved. Moreover, the functionality of a given block of the flowcharts and/or block diagrams may be separated into multiple blocks and/or the functionality of two or more blocks of the flowcharts and/or block diagrams may be at least partially integrated.

In the drawings and specification, there have been disclosed exemplary embodiments of the invention. However, many variations and modifications can be made to these embodiments without substantially departing from the principles of the present invention. Accordingly, although specific terms are used, they are used in a generic and descriptive sense only and not for purposes of limitation, the scope of the invention being defined by the following claims.

That which is claimed is:

1. A method for analyzing a set of images, wherein the images are acquired using at least one image acquisition system and stored such as to be accessible through query to a database, the method comprising:
  receiving a plurality of images from at least one image acquisition system;
  storing the received plurality of images in a data storage system, wherein the images are accessible through query to a database;
  selecting at least a portion of the set of images through query to a database for analysis using at least one attribute of image metadata in the query;
  selecting at least one method for deriving quantitative information from the at least a portion of the set of images;
  processing the selected at least a portion of the set of images with the selected at least one method for deriving quantitative information;
  associating the derived quantitative information with the at least a portion of the set of images via a data structure;
  selecting at least one method for aggregating at least a portion of a set of derived quantitative information into a reduced set of results;
  generating at least one report to represent the reduced set of results for one of an individual image and the set of images as a pool;
  marking a structural measurement, a functional measurement, a descriptor and/or an annotation; and
  identifying one of a boundary of a layer, an area and a volume within the structure of the image,
  wherein the method involves user intervention with a representation of the image displayed on graphical display; is fully automated through computer algorithms without user intervention; or involves a combination of user intervention and computer algorithms;
  wherein the reduced set of results comprises a measurement of distances between boundaries identified within the structure of an image and a statistical summarization of the measurement data according to a sector map defined for the image;
  wherein the statistical summarization comprises one or more of a count, an average, a variance, a standard deviation, and a higher order moment and the computation of a confidence interval; and
  wherein the confidence interval expresses a measure of a degree of goodness of the performance of an algorithm used to generate the reduced results.

2. The method of claim 1, wherein the at least one images acquisition system comprises at least one Optical Coherence Tomography (OCT) imaging system.

3. The method of claim 2, wherein the at least one OCT imaging system comprises at least one Fourier Domain Optical Coherence Tomography imaging System.

4. The method of claim 1, wherein the image metadata comprises one or more of:
  a patient demographic data;
  an individual responsible for drawing inferences from the data;
  an individual responsible for acquiring the images;
  a window of time for acquiring the images;
  a position in a sequence of events along which images may be acquired;
  a descriptor of instruments that may be used to acquire the image data;
  a descriptor of instrument settings used to acquire an image;
  a descriptor of image quality associated with an image;
  quantitative results derived from the image;
  an inference applied to the image; and
  an annotation associated with an image.

5. The method of claim 1, further comprising identifying one or more regions of relative motion within the structure of the image.

6. The method of claim 1, further comprising computing a flow within a region represented by the image.

7. The method of claim 1, further comprising computing a descriptor of a portion of an image, wherein the descriptor comprises one or more of a signal-to-noise ratio, an average noise, a noise variance, a distortion, an attribute histogram and a texture map.

8. The method of claim 1, wherein the data structure comprises one or more of a database, a file structure, and a spreadsheet.

9. The method of claim 1, wherein the report is derived from pooled statistical results from more than one image drawn from the image set.

10. The method of claim 1, wherein the sector map comprises one or more of a regular grid, a volumetric matrix, and a defined grid associated with a clinical or other standard.

11. The method of claim 1, wherein the report comprises one or more of a data table; a two dimensional projection of volumetric data onto a plane; a heat map that associates a color or a gray-scale map to a two dimensional projection of reduced data values onto a plane; a spreadsheet of values, derived from the image; and a spreadsheet of reduced values derived from image.

12. The method of claim 1, wherein the at least one images acquisition system comprises at least one Fourier Domain Optical Coherence Tomography imaging System and wherein the Fourier Domain Optical Coherence Tomography images are images of a region of an eye.

13. The method of claim 12, wherein the region of the eye is selected from one of an anterior segment, cornea, a sclera, a crystalline lens, an iris, an iridocorneal angle, an implanted intraocular lens, a posterior segment, a retina, a macula, an optic nerve head, and a peripheral retina.

14. An image analysis system for acquiring, storing, and analyzing images, the system comprising:
   an image acquisition system configured to acquire and store a plurality of images;
   a database for storing metadata associated with a plurality of images;
   a query system for retrieving stored images based on one or more metadata filters;
   an image analysis module configured to:
   receive a plurality of images from at least one image acquisition system based on a query to the database;
   select at least a portion of a set of images for analysis using at least one attribute of image metadata;
   select at least one method for deriving quantitative information from the at least a portion of the set of images;
   process the selected at least a portion of the set of images with the selected at least one method for deriving quantitative information;
   associate the derived quantitative information with the at least a portion of the set of images via a data structure;
   select at least one method for aggregating at least a portion of a set of derived quantitative information into a reduced set of results;
   generate at least one report to represent the reduced set of results for one of an individual image and the set of images as a pool;
   mark one of a structural measurement, a functional measurement, a descriptor and an annotation; and
   identify one of a boundary of a layer, an area and a volume within the structure of the image,
   wherein the image analysis module is configured to perform functions thereof using user intervention with a representation of the image displayed on graphical display;
   automatically using computer algorithms without user intervention; using a combination of user intervention and computer algorithms;
   wherein the reduced set of results comprises a measurement of distances between boundaries identified within the structure of an image and a statistical summarization of the measurement data according to a sector map defined for the image;
   wherein the statistical summarization comprises one or more of a count, an average, a variance, a standard deviation, and a higher order moment and the computation of a confidence interval; and
   wherein the confidence interval expresses a measure of a degree of goodness of the performance of an algorithm used to generate the reduced results.

15. A computer program product for analyzing a set of images, wherein the images are acquired using at least one an image acquisition system and stored such as to be accessible through query to a database, the computer program product comprising:
   a non-transitory computer-readable storage medium having computer-readable program code embodied in the medium, the computer-readable program code comprising:
   computer readable program code configured to receive a plurality of images from at least one image acquisition system;
   computer readable program code configured to store the received plurality of images in a data storage system, wherein the images are accessible through query to a database;
   computer readable program code configured to select at least a portion of the set of images through query to a database for analysis using at least one attribute of image metadata in the query;
   computer readable program code configured to select at least one method for deriving quantitative information from the at least a portion of the set of images;
   computer readable program code configured to process the selected at least a portion of the set of images with the selected at least one method for deriving quantitative information;
   computer readable program code configured to associate the derived quantitative information with the at least a portion of the set of images via a data structure;
   computer readable program code configured to select at least one method for aggregating at least a portion of a set of derived quantitative information into a reduced set of results;
   computer readable program code configured to generate at least one report to represent the reduced set of results for one of an individual image and the set of images as a pool;
   computer readable program code configured to mark one of a structural measurement, a functional measurement, a descriptor, and an annotation;
   computer readable program code configured to involve user intervention with a representation of the image displayed on graphical display; be fully automated through computer algorithms without user intervention; or to involve both user intervention and computer algorithms; and
   computer readable program code configured to identify a boundary of a layer, an area and/or a volume within the structure of the image,
   wherein the reduced set of results comprises a measurement of distances between boundaries identified within the structure of an image and a statistical summarization of the measurement data according to a sector map defined for the image;

wherein the statistical summarization comprises one or more of a count, an average, a variance, a standard deviation, and a higher order moment and the computation of a confidence interval; and wherein the confidence interval expresses a measure of a degree of goodness of the performance of an algorithm used to generate the reduced results.

\* \* \* \* \*

UNITED STATES PATENT AND TRADEMARK OFFICE
CERTIFICATE OF CORRECTION

PATENT NO. : 9,177,102 B2
APPLICATION NO. : 13/459866
DATED : November 3, 2015
INVENTOR(S) : Bower et al.

It is certified that error appears in the above-identified patent and that said Letters Patent is hereby corrected as shown below:

In the Claims:
Column 19, Claim 14, Line 64: Please correct "play;
　　　automatically using computer algorithms"
to read as one continuous paragraph as follows:
　　-- play; automatically using computer algorithms --

Column 19, Claim 14, Line 66: Please correct "intervention; using a"
　　　to read -- intervention; or using a --

Signed and Sealed this
Seventh Day of June, 2016

Michelle K. Lee
*Director of the United States Patent and Trademark Office*